US007402306B1

(12) United States Patent
Cohen

(10) Patent No.: US 7,402,306 B1
(45) Date of Patent: Jul. 22, 2008

(54) CANCER IMMUNOTHERAPY WITH SEMI-ALLOGENEIC CELLS

(75) Inventor: Edward P. Cohen, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/522,716

(22) Filed: Mar. 10, 2000

Related U.S. Application Data

(62) Division of application No. 09/016,528, filed on Jan. 30, 1998, now Pat. No. 6,187,307.

(60) Provisional application No. 60/036,620, filed on Jan. 31, 1997.

(51) Int. Cl.
*A61K 35/00* (2006.01)
*C12N 15/85* (2006.01)

(52) U.S. Cl. .................... 424/93.1; 435/325

(58) Field of Classification Search ........... 424/93.1, 424/93.21, 93.71; 435/325, 455, 366, 372
See application file for complete search history.

(56) References Cited

U.S. PATENT DOCUMENTS

| 5,674,486 | A | 10/1997 | Sobol et al. | |
|---|---|---|---|---|
| 5,750,102 | A * | 5/1998 | Eisenbach et al. | |
| 6,022,538 | A | 2/2000 | Santoli et al. | |
| 6,228,357 | B1 | 5/2001 | Maudsley | |
| 6,277,368 | B1 * | 8/2001 | Hiserodt et al. | 424/93.21 |
| 6,805,869 | B2 | 10/2004 | Guo | |
| 7,060,802 | B1 | 6/2006 | Trakht et al. | |
| 2002/0058041 | A1 | 5/2002 | Belldegrun et al. | |
| 2002/0085997 | A1 * | 7/2002 | Schmidt et al. | 424/93.21 |

FOREIGN PATENT DOCUMENTS

| EP | 0 569 678 A2 * | 11/1993 |
|---|---|---|
| EP | 0569678 A2 | 11/1993 |
| WO | 9307906 | 4/1993 |
| WO | 9811202 | 3/1998 |
| WO | WO 98/11202 | 3/1998 |
| WO | WO 98/14205 | 4/1998 |

OTHER PUBLICATIONS

Evans et al Quart. J. Med. vol. 92 pp. 299-307, 1999.*
Lappin MB et al Blood Reviews 2000 14:228-239.*
Roitt et al Immunology 4th ed. 1998 pp. 11.7-11.14.*
Weiner L.M., Seminars Oncology, vol. 26, No. 4, Suppl 12, pp. 41-50, 1999.*
Bellone et al. . (Immunology Today, v20 (10), 1999, pp. 457-462).*
Gura (Science, v278, 1997, pp. 1041-1042).*
Sun T. et al. Cancer Gene Therapy 2(3): 183-190, 1995.*
D.L. Shawler et al. (1997) "Gene Therapy Approaches to Enhance Antitumor Immunity" *Advances in Pharmacology 40:* 309-337.
T. Boon et al. (1992) "Identification of Tumor Rejection Antigens Recognized By T-Lymphocytes" *Cancer Surveys 13:* 23-37.
T. Boon (1993) "Tumor Antigens Recognized By Cytolytic T Lymphocytes: Present Perspectives for Specific Immunotherapy" *Int. J. Cancer 54:* 177-180.
T. Boon (1992) "Toward a Genetic Analysis of Tumor Rejection Antigens" *Advances in Cancer Research 58:* 177-209.
J. Vieweg and E. Gilboa (1995) "Considerations for the Use of Cytokine-Secreting Tumor Cell Preparations for Cancer Treatment" *Cancer Investigation:* 13 (2): 193-201.
K.M. Hui et al. (1989) "Tumor Rejection Mediated by Transfection With Allogeneic Class I Histocompatibility Gene" *The Journal of Immunology 143* (11): 3835-3843.
S. Ostrand-Rosenberg et al. (1991) "Tumor-Specific Immunity Can Be Enhanced By Transfection of Tumor Cells With Syngeneic MHC-Class-II Genes or Allogeneic MHC-Class-I Genes" *Int. J. Cancer 6* (Supp.): 61-68.
J.A. Roth and R.J. Cristiano (1997) "Gene Therapy for Cancer: What Have We Done and Where Are We Going?" *Journal of the National Cancer Institute 89* (1): 21-39.
T.S. Kim and E.P. Cohen (1994) "MHC Antigen Expression By Melanomas Recovered From Mice Treated With Allogeneic Mouse Fibroblasts Genetically Modified for Interleukin-2 Secretion and the Expression of Melanoma-associated Antigens" *Cancer Immunol. Immunother.* (1994) 38: 185-193.
T.S. Kim et al. (1992) "Immunity to B16 Melanoma in Mice Immunized With IL-2-secreting Allogeneic Mouse Fibroblasts Expressing Melanoma-associated Antigens" *Int. J. Cancer 51:* 283-289.
E.P. Cohen and T.S. Kim (1994) "Neoplastic Cells That Express Low Levels of MHC Class I Determinants Escape Host Immunity" *Seminars in Cancer Biology 5:* 419-428.
T. Itaya et al. (1987) "Xenogenization of a Mouse Lung Carcinoma (3LL) By Transfection With An Allogeneic Class I Major Histocompatibility Complex Gene $(H-2L^d)^1$" *Cancer Research 47:* 3136-3140.
T. Lichtor et al. (1995) "Prolonged Survival of Mice With Glioma Injected Intracerebrally With Double Cytokine-secreting Cells" *J. Neurosurg. 83:* 1038-1044.
P. van der Bruggen et al. (1991) "A Gene Encoding an Antigen Recognized By Cytolytic T Lymphocytes on a Human Melanoma" *Science 254:* 1643-1647.
D.L. Toffaletti et al. (1983) "Augmentation of Syngeneic Tumor-specific Immunity By Semiallogeneic Cells Hybrids" *The Journal of Immunology 130* (6): 2982-2986.
M. I. Colnaghi (1975) "Histocompatibility Antigens Acting as Helper Determinants for Tumor-associated Antigens of Murine Lymphosarcoma" *Eur. J. Immunol. 5:* 241-245.
W. Xu et al. (1998) "Co-expression of Immunogenic Determinants by the Same Cellular Immunogen is Required for the Optimum Immunotherapeutic Benefit in Mice With Melanoma" *Cancer Immunol. Immunother. 45:* 217-224.

(Continued)

*Primary Examiner*—Christopher Yaen
(74) *Attorney, Agent, or Firm*—McDonnell Boehnen Hulbert & Berghoff LLP

(57) ABSTRACT

The present invention relates to improved semi-allogeneic immunogenic cells which act to stimulate and induce an immunological response when administered to an individual. In particular, it relates to cells which express both allogeneic and syngeneic MHC determinants and which also express at least one antigen recognized by T lymphocytes. The invention is also directed to methods of inducing an immune response and methods of treating tumors by administering the semi-allogeneic immunogenic cells to an individual.

15 Claims, 19 Drawing Sheets

OTHER PUBLICATIONS

D.R. Wang et al. (1985) "Leukemia x Fibroblast Hybrid Cells Prolong the Lives of Leukemic Mice" *Eur. J. Cancer Clin. Oncol. 21* (5): 637-645.

W. Liang and E.P. Cohen (1976) "Resistance to Murine Leukemia in Mice Rejecting Syngeneic Somatic Hybrid Cells" *The Journal of Immunology 116* (3): 623-626.

W. Liang and E.P. Cohen (1977) "Activation of Specific Cellular Immunity Toward Murine Leukemia in Mice Rejecting Syngeneic Somatic Hybrid Cells" *The Journal of Immunology 119* (3): 1054-1060.

B.S. Kim et al. (1979) "Tumor-specific Immunity Induced by Somatic Hybrids" *The Journal of Immunology 123* (2): 733-738.

S.L. Garber et al. (1984) "Persistence of the Immunoprotective Effects of Leukemia x Fibroblast Hybrid Cells Toward Leukemia in Histocompatible Mice" *Leukemia Research 8* (2): 255-266.

R. Slomski et al. (1984) "Surface Antigens of Immunoprotective Leukaemia x Fibroblast Hybrid Cells Which Have Lost Malignant Properties in Histocompatible Mice Differ From the Malignant Parental Cells" *Immunology 52:* 281-290.

W. Liang and E.P. Cohen (1977) "Resistance to Murine Leukemia in Mice Receiving Simultaneous Injections of Syngeneic Hybrid and Parental Neoplastic Cells" *The Journal of Immunology 118* (3): 903-908.

J. Jami and E. Ritz (1975) "Tumor-associated Transplantation Antigens in Immune Rejection of Mouse Malignant Cell Hybrids" *Proc. Nat. Acad. Sci. USA 72* (6): 2130-2134.

J. Jami and E. Ritz (1973) "Nonmalignancy of Hybrids Derived From Two Mouse Malignant Cells. I. Hybrids Between L1210 Leukemia Cells and Malignant L. Cells" *Journal of the National Cancer Institute 51*(5): 1647-1653.

S.E. Karp et al. (1993) "Cytokine Secretion By Genetically Modified Nonimmunogeneic Murine Fibrosarcoma Tumor Inhibition by IL-2 but Not Tumor Necrosis Factor" *The Journal of Immunology 150* (3): 896-908.

T.S. Kim et al. (1993) "Independent Cell Types Are Involved in the Induction of Antimelanoma Responses in C57BL/6 Mice Immunized with Interleukin-2-secreting Allogeneic Mouse Fibroblasts Expressing Melanoma-associated Antigens" *Journal of Immunotherapy 14:* 298-304.

T.S. Kim et al. (1993) "Immunization With Interleukin-2-secreting Allogeneic Mouse Fibroblasts Expressing Melanoma-associated Antigens Prolongs the Survival of Mice With Melanoma" *Int. J. Cancer 55:* 865-872.

D.M. Pardoll (1993) "Cancer Vaccines" *Immunology Today 14* (6): 310-316.

D. Pardoll (1992) "New Strategies for Active Immunotherapy With Genetically Engineered Tumor Cells" *Current Opinion in Immunology 4:* 619-623.

A. Porgador et al. (1993) "Antimetastatic Vaccination of Tumor-bearing Mice With Two Types of IFN-λ Gene-inserted Tumor Cells" *The Journal of Immunology 150* (4): 1458-1470.

A. Porgador et al. (1993) "Anti-metastatic Vaccination of Tumor-bearing Mice With IL-2-Gene-inserted Tumor Cells" *Int. J. Cancer 53:* 471-477.

A. Porgador et al. (1992) "Interleukin 6 Gene Transfection into Lewis Lung Carcinoma Tumor Cells Suppresses the Malignant Phenotype and Confers Immunotherapeutic Competence Against Parental Metastatic Cells" *Cancer Research 52:* 3679-3686.

S.A. Rosenberg (1992) "The Immunotherapy and Gene Therapy of Cancer" *Journal of Clinical Oncology 10*(2): 180-199.

S.J. Russell et al. (1991) "Decreased Tumorigenicity of a Transplantable Rat Sarcoma Following Transfer and Expression of an IL-2 cDNA" *Int. J. Cancer 47:* 244-251.

J.S. Weber and S.A. Rosenberg (1988) "Modulation of Murine Tumor Major Histocompatibility Antigens by Cytokines in Vivo and in Vitro" *Cancer Research 48:* 5818-5824.

G. Yamada et al. (1987) "Retroviral Expression of the Human IL-2 Gene in a Murine T-Cell Line Results in Cell Growth Autonomy and Tumorigenicity" *The EMBO Journal 6* (9): 2705-2709.

M. Zöller et al. (1988) "Interferon-gamma Treatment of B16 Melanoma Cells: Opposing Effects for Non-adaptive and Adaptive Immune Defense and its Reflection by Metastatic Spread" *Int. J. Cancer 41:* 256-266.

M. Kasai et al. (1980) "A Glycolipid on the Surface of Mouse Natural Killer Cells" *Eur. J. Immunol. 10:* 175-180.

H.F. Oettgen et al. (1990) "Serologic Analysis of Human Cancer" *Immunol. Allergy Clin. North. Am. 10* (4): 607-637.

M. Sarmiento et al. (1985) "IgG or IgM Monoclonal Antibodies Reactive With Different Determinants on the Molecular Complex Bearing LYT 2 Antigen Block T Cell-mediated Cytolysis in the Absence of Complement" *J. Immunol. 125* (6): 2665-2672.

B. Sugden et al. (1985) "A Vector That Replicates as a Plasmid and Can Be Efficiently Selected in B-Lymphoblasts Transformed by Epstein-Barr Virus" *Mol. Cell. Biol. 5* (2) : 410-413.

C. Traversari et al. (1992) "A Nonapeptide Encoded by Human Gene MAGE-1 Is Recognized on HLA-A1 by Cytolytic T Lymphocytes Directed Against Tumor Antigen MZ2-E" *J. Exp. Med. 176:* 1453-1457.

R.G. Vile and I.R. Hart (1993) "In Vitro and in Vivo Targeting of Gene Expression to Melanoma Cells" *Cancer Res. 53:* 962-967.

M. Wigler et al. (1978) "Biochemical Transfer of Single-copy Eucaryotic Genes Using Total Cellular DNA as Donor" *Cell 14:* 725-731.

H.E. Young et al. (1995) "Mesenchymal Stem Cells Reside Within the Connective Tissues of Many Organs" *Dev. Dynamics 202:* 137-144.

J. Vieweg et al. (1995) "Considerations for the Use of Cytokine-secreting Tumour Cell Preparations for Cancer Treatment" *Cancer Investigation 13*(2): 193-201.

X. Wu et al. (1998) "Co-expression of Immunogenic Determinants by the Same Cellular Immunogen is Required for the Optimum Immunotherapeutic Benefit in Mice Melanoma" *Cancer Immunol. Immunother. 45* (5): 217-224.

D.A. Newton et al. (1997) "Melanoma Cell Hybrids as Cancer Vaccines" *Proceedings of the Annual Meeting of the American Association for Cancer Research 38:* 398.

D. L. Toffaletti et al. (1983) "Augmentation of Syngeneic Tumor-specific Immunity by Semiallogeneic Cell Hybrids" *Journal of Immunology 130* (6): 2982-2986.

B. Payelle et al. (1981) "Adoptive Transfer of Immunity Induced by Semi-allogeneic Hybrid Cells Against Murine Fibrosarcoma" *Int. J. Cancer 27:* 783-788.

O. Mandelbiom et al. (1995) "Expression of two H-2K genes, syngeneic and allogeneic, as a strategy for potentiating immune recognition of tumor cells" *Gene Therapy 2:* 757-765.

Marshall, Science, 269:1050-1055, 1995.

Miller et al., FASEB J., 9:190-199, 1995.

Culver et al., TIG, 10(5): 174-179, 1994.

Blankstein, T. et al., Tumor Suppression after Tumor Cell-targeted Tumor Necrosis Factor alpha Gene Transfer. J. Exp. Med., 173: 1047-1052 (1991).

Colombu, M. et al., Granulocyte Colony-stimulating Factor Gene Transfer Suppresses Tumorigenicity of a Murine Adenocarcinoma In Vivo, J. Exp. Med., 173: 889-897 (1991).

Dranoff, G. et al., Vaccination with irradiated tumor cells engineered to secret murine granulocyte-macrophage colony-stimulating factor stimulates potent, specific, and long-lasting anti-tumor immunity, Proc. Natl. Acad. Sci. USA, 90: 3539-3543 (1993).

Fearon, E.R. et al., Interleukin-2 Production by Tumor Cells Bypasses T Helper Function in the Generation of an Anti-tumor Response, Cell, 60: 397-403 (1990).

Ferrantini, M. et al., alpha 1-Interferon Gene Transfer into Metastatic Friend Leukemia Cells Abrogated Tumorigenicity in Immunocompetent Mice: Antitumor Therapy by Means of Interferon-producing Cells, Cancer Res., 53: 1107-1112 (1993).

Golumbek, P. et al., Treatment of Established Renal Cancer by Tumor Cells Engineered to Secrete Interleukin-4, Science, 254: 713-716 (1991).

Karp, S.E. et al., Cytokin Secretion by Genetically Modified Nonimmunogenic Murine Fibrosarcoma, J. Immunol., 150: 896-908 (1993).

Kim et al., Cancer Immunol. Immunother. 1991, 34:163-168.

Kim et al., Cancer Research, 1994, 54:2531-2535.

Hodgson, Expert Opinion on Therapeutic Patents, 5(5):459-468, 1995.

Nih, pp. 1-37, Dec. 7, 1995.

Kim, T., et al., "Immunity To B16 Melanoma In Mice Immunized With IL-2 Secreting Allogeneic Mouse Fibroblasts Expressing Melanoma-Associated Antigens," Int. J. Cancer, vol. 51, pp. 283-289 (1992).

Schmidt, W., et al., "Transloading of Tumor Cells With Foreign Major Histocompatibility Complex Class I Peptide Ligand: A Novel General Strategy For The Generation of Potent Cancer Vaccines," Proc. Natl. Acad. Sci USA, vol. 93, pp. 9759-9763 (1996).

* cited by examiner

Days after injection of EO771 cells

CANCER IMMUNOTHERAPY WITH SEMI-ALLOGENEIC CELLS

CROSS-REFERENCE TO RELATED APPLICATION

This application is a divisional of application Ser. No. 09/016,528, filed on Jan. 30, 1998 now U.S. Pat. No. 6,187, 307, which claims the benefit of Provisional Application Ser. No. 60/036,620, filed Jan. 31, 1997.

STATEMENT REGARDING GOVERNMENT SPONSORSHIP

This invention was made with United States government support under Grant No. RO1-CA-55651-02 awarded by the National Institutes of Health. The United States government may have certain rights in the invention.

BACKGROUND OF THE INVENTION

1. Field of the Invention

The present invention relates to improved semi-allogeneic immunogenic cells which act to stimulate and induce an immunological response when administered to an individual. In particular, it relates to cells which express both allogeneic and syngeneic MHC determinants and which also express at least one antigen recognized by T lymphocytes. The invention is also directed to methods of inducing an immune response and methods of treating tumors by administering the semi-allogeneic immunogenic cells to an individual.

2. State of the Prior Art

T lymphocytes recognize an extraordinarily wide array of relatively small peptides derived from larger macromolecules in the context of membrane-associated structures specified by the class-I major histocompatibility complex (MHC).

Most progressively growing neoplastic cells form potential immunogenic tumor associated antigens (TAAs). TAAs have been identified for a number of tumors, including melanoma, breast adenocarcioma, prostatic adenocarcinoma, esophageal cancer, lymphoma, and many others. See review by Shawler et al. *Advance in Pharmacology* 40:309-337, Academic Press (1997). Like other epitopes, TAAs on tumor cells are recognized by T lymphocytes in the context of MHC-specified determinants. Traversari et al. (1992) *J. Exp. Med.* 176:1453-1457; van.der Bruggen et al. (1991) *Science* 254:1643-1647. However, such tumor cells do not provoke anti-tumor immune responses that are capable of controlling the growth of malignant cells. Boon et al. (1992) *Cancer Surveys* 13:23-37; Boon, T. (1993) *Int. J. Cancer* 54:177-180; Boon, T. (1992) *Advances Cancer Res.* 58:177-209.

In recent years, attention has focused on the use of cytokines in an attempt to augment the immune response to tumor-associated antigens. Cytokines such as interleukin 2 (IL-2) or interferon (IFN-γ) have been used to treat neoplastic disease with marginal therapeutic impact. Vieweg et al. (1995) *Cancer Investigation* 132(2):193-201. Cytokines do not exhibit direct toxic effect on cancer cells; their anti-tumor activity is mediated by modulation of the host's immunological response to the neoplasm. For example, interferon-y induces the expression of MHC class I determinants and augments the sensitivity of tumor cells to cytotoxic T cell-mediated lysis. Lichtor et al. (1995) *J. Neurosurg* 83:1038-1044. IL-2 is required for the growth of cytotoxic T lymphocytes and enhances natural killer (NK) and lymphokine-activated killer cells (LAK). The limited effect of systemic administration of IL-2 in cancer immunotherapy has been partially explained by the short half-life of IL-2 and severe toxicity due to necessary high doses. Vieweg et al. (1995).

Lymphokine-activated killer cells (LAK) have also been used as an approach to elicit a cellular immune response. LAK cells are MHC-unrestricted lymphoid cells which kill fresh tumor cells but not normal cells. Tumor-infiltrating lymphocytes (TIL) are predominantly MHC-restricted T cells which have been found to be 50-100 times more potent than LAK cells in murine models. The use of LAK or TIL either alone or with IL-2 has shown some anti-tumor effects. In the combined approach however, IL-2 toxicity remains a problem. Vieweg et al. (1995).

More recently, immunotherapy of neoplastic disease has involved the introduction of genes for cytokines into autologous malignant cells which are then introduced into immunocompetent recipients. The introduction and expression of the gene for IL-2 or IFN-γ into a tumor cell, usually by retroviral transduction, results in recognition of the cells by the immune system, a decrease in the cells' metastatic properties and the generation of immune responses that are capable of causing the rejection of both cytokine-secreting and the original cytokine non-secreting tumor cells. As occurs with other therapeutic strategies, elimination of the entire neoplastic cell population is often incomplete and tumor growth recurs. Cohen et al. (1994) *Seminars in Cancer Biology* 5:419-428.

In related studies, the introduction of genes specifying defined, but allogeneic (foreign to the recipient) MHC class I determinants into murine tumor cells leads to a loss of the cells' tumorigenicity in immunocompetent recipients. Similar to tumor cells which have been modified for cytokine secretion, mice rejecting tumor cells expressing both syngeneic and allogeneic antigens express immunity toward unmodified neoplasms expressing syngeneic determinants alone. Survival of tumor-bearing mice immunized with the modified cells is significantly longer than that of nonimmunized mice, although in most instances, tumor growth recurs and the animals Ieventually succumb to the disease. Itaya et al. (1987) *Cancer Res.* 47:3136-3140; Hui et al. (1989) *J. Imunol.* 143:3835-43; Ostrand-Rosenberg (1991) *Int. J. Cancer* [Suppl] 6:61-8.

Modification of tumor cells for purposes of immunotherapy requires establishment of a cell line from the patient's malignant cells. Establishing such a cell line cannot always be accomplished, as is shown by, e.g., Oettgen, et al., *Immunol. Allergy. Clin. North. Am.* 10:607-637 (1990). In addition, malignant cells isolated from a patient which are capable of growing in vitro may not be reflective of the patient's neoplasm as a whole. That is, tumor associated antigens present on only a small population of cells may not be included in cells which are capable of growing in vitro. Moreover, in those rare instances where a long term malignant cell line can be established, transduction of cell lines and post transduction selection can result in selective loss of tumor associated antigens expressed by the parental malignant cells in vivo.

Recent studies in cancer immunotherapies have involved the use of allogeneic cells such as mouse fibroblasts which have been genetically engineered to express (antibody-defined) melanoma-associated.antigens (MAAs) and to secrete IL-2. Mice with established melanoma and immunized with the modified fibroblasts develop strong cellular anti-melanoma immune responses, mediated primarily by CD8$^+$ T-cells, macrophages and natural killer/lymphokine-activated killer (NK/LAK) cells. Immunized mice survive significantly longer than both nonimmunized mice and mice immunized with irradiated melanoma cells. Kim et al. (1992) *Int. J. Cancer* 51:283-289.

Two nonexclusive mechanisms have been proposed to explain the improved response against autologous tumors in mice immunized with allogeneic cells engineered to secrete IL-2 and express MAAs:(i) large numbers of CTLs with specificity toward tumor-associated antigens expressed by the neoplasm are generated in the micro environment of allograft recognition and rejection (the immunogenic properties of tumor cells transfected with genes specifying allogenic determinants is supportive, Hui et al. (1989) *J. Immunol.* 143:3835-3843; Ostrand-Rosenberg et al. (1991) *J. Cancer* 6:[Suppl.]:61-680); and (ii) allogeneic MHC class I determinants present tumor-associated T-cell epitopes directly to CTL precursors. The high, local environment of IL-2, secreted by the genetically modified cells, further augments the generation of large numbers of CTLs with anti-tumor specificity.

Although survival of tumor-bearing mice treated with IL-2 secreting, TAA expressing, allogeneic cells is significantly (P<0.001) longer than that of untreated mice, in most instances the tumor cell population is incompletely eradicated and the mice eventually die from progressive malignant melanoma. Kim et al. (1994) *Cancer Immunol. Immunother.* 38:185-193. The state of gene therapy is generally assessed by Roth and Cristiano, *J. National Cancer Institute* 89(1): 21-39 (1997), however, significant obstacles in cancer immunotherapy have yet to be overcome.

Accordingly, there is a need for more effective cellular immunogenic cells which elicit stronger and longer lasting T-cell mediated immune responses against cancerous cells in the body.

SUMMARY OF THE INVENTION

The present invention is directed to semi-allogeneic immunogenic cells genetically selected which express at least one class I MHC or class II MHC determinant that is syngeneic to a recipient, at least one class I or class II MHC determinant that is allogeneic to the recipient, and at least one antigen recognized by T cells.

In one aspect of the invention, the semi-allogeneic immunogenic cells comprise an antigen presenting cell expressing at least one of class I or class II MHC determinants wherein at least one class I MHC or class II MHC determinant is syngeneic to a recipient and wherein at least one of the class I or class II MHC determinants expressed by the antigen presenting cell is allogeneic to the recipient, and wherein said antigen presenting cell is transformed with and expresses nucleic acid molecules coding for at least one antigen recognized by T cells.

In one embodiment of the invention, the nucleic acid molecules coding for at least one antigen recognized by T cells comprise a known coding sequence for an antigen recognized by T cells. The coding sequences contemplated by the present invention include coding sequences from an infectious agent, such as a bacterium, virus, or parasite, as well as coding sequences for tumor associated antigens (TAAs).

The preferred coding sequences of the present invention are those coding for tumor associated antigens (TAAs). A number of known TAA-coding sequences may be used for such purposes, which include but are not limited to genes of the MAGE family, BAGE, Tyrosinase, CEA, CO17-1A, MART-1, gp100, MUC-1, TAG-72, CA 125, Decapeptide 810, P1A; mutated proto-oncogenes such as $p21^{ras}$, P210 gene, and HER-2/neu; mutated tumor suppressor genes such as p53; (4) tumor associated viral antigens such as HPV16 E7. Such genes are amply described in the literature; e.g., Shawler et al. (1997).

In another embodiment of the present invention, the nucleic acid molecules coding for at least one antigen recognized by T cells comprise genomic DNA or RNA isolated from an infectious agent, such as a bacterium, virus or parasite, or from tumor cells. According to the present invention, the tumor cells used for isolating DNA or RNA may include cells from a tumor cell line, as well as cells from a neoplasm or a tumor of a recipient. Many tumor cell lines are available for this purpose, such as mouse B16 melanoma cells, mouse EO771 mammary adenocarcinoma cells and human tumor cell lines. Preferably, the tumor cells from which the DNA or RNA is isolated are obtained from a solid or diffuse neoplasm (i.e., solid or hematological tumor) of a recipient. The neoplasms include but are not limited to melanoma, lymphoma, plasmocytoma, sarcoma, glioma, thymoma, leukemias, breast cancer, prostate cancer, colon cancer, esophageal cancer, brain cancer, lung cancer, ovary cancer, cervical cancer, hepatoma, and other neoplasms known in the art, such as those described by Shawler et al. (1997).

In another aspect of the invention, the semi-allogeneic immunogenic cells comprise a semi-allogeneic hybrid cell formed by fusing an antigen presenting cell with a tumor cell, wherein the hybrid cell expresses at least one class I MHC or class II MHC determinant that is syngeneic to a recipient and at least one class I or class II MHC determinant that is allogeneic to the recipient, and wherein the hybrid cell also expresses at least one antigen recognized by T cells. In a preferred embodiment, the antigen expressed by the semi-allogeneic hybrid cell that is recognized by T cells is a tumor associated antigen.

According to the present invention, all the tumor cells as described hereinabove may be employed in such cell fusion, including cells from a tumor cell line, as well as cells from a tumor of a recipient. Preferably, the tumor cells are obtained from a solid or diffuse neoplasm (i.e., solid or hematological tumor) of a recipient. The neoplasms include but are not limited to melanoma, lymphoma, plasmocytoma, sarcoma, glioma, thymoma, leukemias, breast cancer, prostate cancer, colon cancer, esophageal cancer, brain cancer, lung cancer, ovary cancer, cervical cancer, hepatoma, and other neoplasms known in the art, such as those described by Shawler et al. (1997).

In a further aspect of the invention, the semi-allogeneic immunogenic cells are also transformed by and express a nucleic acid sequence coding for at least one cytokine.

A still further aspect of the invention is directed to therapeutic compositions comprising the subject semi-allogeneic immunogenic cells.

Another aspect of the invention provides methods for inducing an immunological response which comprises administering to an animal in need of such response an immunologically effective amount of the subject semi-allogeneic immunogenic cells.

The present invention also provides methods of preventing or treating a tumor in an animal which comprise administering to said animal an anti-tumor effective amount of the immunogen prepared in accordance with the present invention.

BRIEF DESCRIPTION OF THE DRAWINGS

These and other features, aspects, and advantages of the compositions and methods of the present invention will become better understood with regard to the following description, appended claims, and accompanying drawings. As used herein, the symbol "/" denotes that the relevant cells are transfected with genomic DNA, while the symbol "x"

denotes that the relevant cells are fused resulting hybrid cells. For example, "LM-IL-$2K^b$/B16" represents LM-IL-$2K^b$ cells are transfected with genomic DNA from B16 cells; "LM (TK−)×B16" represents hybrid cells formed by fusing LM(TK−) cells and B16 cells.

DETAILED DESCRIPTION OF THE INVENTION

Figure 1:
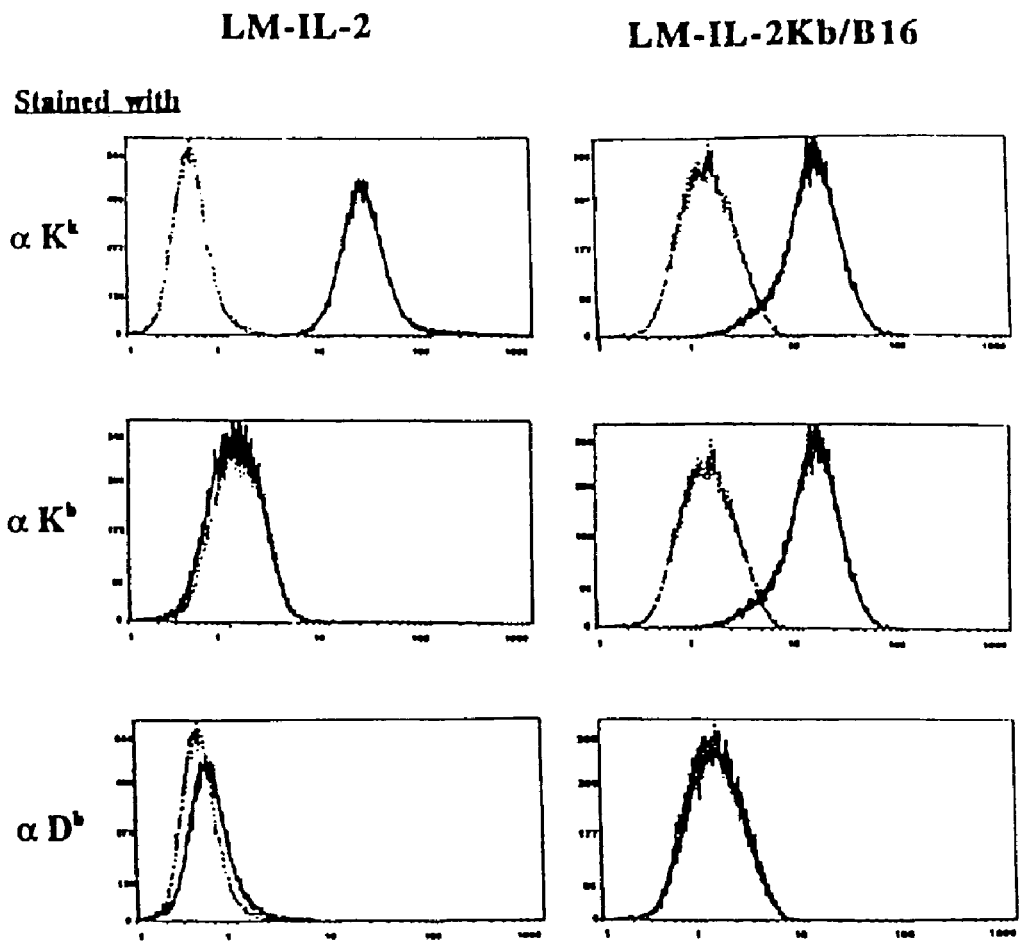
FIG. 1 graphically depicts immuno-fluorescent staining of LM-IL-2 cells transduced with pBR327H-$2K^b$ with mAbs for $H-2K^b$-determinants. The fine line indicates cells incubated with $IgG_{2a}$ isotype serum. The bold line indicates cells incubated with anti-H-$2K^b$, anti-H-$2K^K$, or anti-H-$2D^b$ mAbs.

The present invention is directed to semi-allogeneic immunogenic cells genetically selected which express both allogeneic (foreign to a recipient) and syngeneic (same to the recipient) MHC determinants and also express at least one other antigen which is recognized by T lymphocytes of the recipient and which associates with the allogeneic and syngeneic MHC determinants. The present invention is further directed to therapeutic methods employing the subject semi-allogeneic immunogenic cells.

In accordance with the present invention, it has been surprisingly found that the combined expression of both syngeneic and allogeneic MHC determinants along with the expression of antigens recognized by T cells, stimulates an immunological response of even greater magnitude than immunogenic cells that express either syngeneic or allogeneic MHC determinants alone. For example, the combined expression of both syngeneic and allogeneic MHC class I determinants along with the expression of tumor associated antigens (TAAs) in fibroblast cells provide highly augmented, long-term anti-tumor cellular immune responses in mice immunized with the semi-allogeneic fibroblast cells. In some instances, the animals reject the tumor cells and survive indefinitely.

The semi-allogeneic immunogenic cells of the present invention comprise a cell genetically selected which expresses MHC determinants that are semi-allogeneic to a recipient and which also expresses at least one antigen recognized by T cells.

The term "a cell" or "cells" as used herein refers to singular cells as well as populations of cells.

The term "genetically selected" as used herein denotes cells, e.g., antigen presenting cells, which are selected by genetic approaches to ensure that such cells express MHC determinants that are semi-allogeneic and also express at least one antigen recognized by T cells. The genetic approaches that may be employed include, but are not limited to, HLA typing, transformation or transfection techniques for introducing nucleic acid molecules into the antigen presenting cells, and cell fusion techniques. These techniques are well known in the art and are further described in the disclosure which follows.

Those skilled in the art may appreciate the present invention for the subject semi-allogeneic immunogenic cells genetically selected for immunotherapy. Antigen presenting cells ordinarily express at least one MHC determinant. However, antigen presenting cells ordinarily available may not express MHC determinants that are semi-allogeneic, i.e., these cells may express only allogeneic MHC determinants or only syngeneic determinants. Such antigen presenting cells may be transformed with nucleic acid molecules encoding at least one class I or class II MHC determinant (either syngeneic or allogeneic) such that the transformed antigen presenting cells are selected that express both syngeneic and allogeneic determinants. In other instances, a number of donor antigen presenting cells are available in a bank or a hospital that may or may not express both syngeneic and allogeneic MHC determinants. According to the present invention, appropriate donor cells are selected for immunotherapy that express both allogeneic and syngeneic MHC determinants by, e.g., HLA typing a number of donor cells and the recipient. In other instances, antigen presenting cells that are available may not express at least one antigen recognized by T cells of the recipient. According to the present invention, such antigen presenting cells may then be transformed with DNA coding for at least one antigen recognized by T cells of the recipient. Antigen presenting cells may also be genetically modified by, e.g., a cell fusion process, such that the resulting hybrid cells express at least one syngeneic MHC determinant, at least one allogeneic determinant, and at least one antigen recognized by T cells.

According to the present invention, the antigen presenting cells as referred herein express at least one of class I or class II MHC determinants and may comprise those cells which are known as professional or constitutive antigen-presenting cells such as macrophages, dendritic cells and B cells. Other professional antigen-presenting cells include monocytes, macrophages, marginal zone Kupffer cells, microglia, Langerhans, cells, interdigitating dendritic cells, follicular dendritic cells, and T cells. Facultative antigen-presenting cells may also be used in the immunogenic cells of the present invention. Examples of facultative antigen-presenting cells include astrocytes, follicular cells, endothelium and fibroblasts. As used herein, "antigen-presenting cells" encompass both professional (constitutive) and facultative types of antigen-presenting cells.

It is understood that as used herein the term "fibroblast" also includes those types of cells which develop into fibroblasts such as mesenchymal stem cells, Young et al. (1995) *Dev. Dynamics* 202:137-144.

In one embodiment of the present invention, the facultative antigen-presenting cell is a fibroblast. Human fibroblast cell lines, established from normal fibroblast cells as well as malignant fibroblast cells taken from individuals, may be obtained from the American Type Culture Collection, 12301 Parklawn Drive, Rockville, Md., 20852-1776. Human fibroblasts may also be obtained from infant foreskins after circumcision. Plentiful supplies of infant foreskins are available in infant nurseries of hospitals. Macrophage cell lines and B cell lines are available through the ATCC. Other types of antigen-presenting cells including fibroblasts can be isolated from tissue samples obtained from human-subjects.

The immunogenic cells of the present invention express MHC determinants that are semi-allogeneic to a recipient. "Semi-allogeneic MHC determinants" refers to at least one class I or class II MHC determinant expressed by the subject immunogenic cells is syngeneic to a recipient and at least one class I or class II MHC determinant is allogeneic to the recipient. "Syngeneic" refers to an MHC allele coding for an HLA specificity that matches and is immunologically compatible with at least one of a class I or class II MHC allele of a recipient. "Allogeneic" refers to at least one of a class I or class II MHC allele coding for an HLA specificity that is unmatched and immunologically incompatible with at least one of a class I or class II MHC allele of the recipient.

As described in the literature, the human MHC locus, called HLA, is found on chromosome 6 and contains at least 50 closely-linked genes. There are three classical MHC class I genes, HLA-A, -B, and -C, each of which encodes an a-chain of a MHC class I molecule. The human MHC class II genes are arranged into at least three subregions, HLA-DP, -DQ, and-DR, each of which contains at least one a gene and one f gene, Roitt et al. *Immunology,* 2d ed. Gower Medical Publishing, New York, 1989.

There are a large number of genes in the MHC locus and a great degree of polymorphism within each MHC gene. Thus a normal human population will have a very large number of different genotypes. Table I (taken from Roitt et al.) lists the distinct antigenic specificities detected at each HLA subregion. A haplotype is a set of linked MHC genes on one chromosome 6. Since an individual inherits one maternal and one paternal chromosome 6, one HLA haplotype is derived from each parent.

In mice, the MHC locus (called H-2) is found on chromosome 17. There are three main MHC class I genes, H-2K, H-2D, and H-2L. There are also three main MHC class II genes, H-2A, H-2E and H-2M.

The present invention describes how to genetically modify antigen presenting cells such that these cells express MHC determinants that are semi-allogeneic to a recipient. Under the circumstance that the antigen presenting cell to be used expresses only allogeneic determinants, a nucleic acid molecule coding for at least one syngeneic determinant may be introduced into the antigen presenting cell by well known transfection or transformation procedures, such as those described by Sambrook et al., 1989, Molecular Cloning: *A Laboratory Manual*, Second Edition, Cold Spring Harbor Laboratory Press, New York.

The working Examples describe a method of introducing a gene for a mouse syngeneic MHC class I determinant, H-2$K^b$, into mouse fibroblast cells expressing allogeneic MHC determinants of the k haplotype, i.e., H-2$^k$. (Superscript is used to indicate a haplotype.) When employed in an animal immunotherapy regime such as human immunotherapy, the step of introducing a gene for a human syngeneic MHC determinant into an antigen presenting cell may not always be necessary. Donor antigen presenting cells might be available which have at least one class I or class II MHC determinant that matches with one of the MHC determinants of a recipient. Such antigen presenting cells may be selected after HLA typing the recipient and a number of possible donor antigen-presenting cells.

In accordance with the present invention, HLA typing is performed on an individual who is to be the recipient of the subject semi-allogeneic immunogenic cells in order to determine that individual's HLA type. Methods of HLA typing are well known to those skilled in the art, are performed routinely in hospitals and clinical laboratories and are generally described in Roitt et al.(1989).

In accordance with the present invention, a bank or library may be assembled comprising different human antigen-presenting cell lines which are maintained continuously in culture. Each antigen-presenting cell line is also HLA typed and recorded by any number of record keeping methodologies such as a log book, computer database, etc. After HLA typing a recipient individual, an antigen-presenting cell line is chosen from the library or other source so that at least one allele coding for HLA specificities expressed by the antigen-presenting cell and the recipient is unmatched. Thus, for example, with regard to MHC class I determinants, a recipient having an A subregion specificity of A1-A2 can receive antigen-presenting cells having an A subregion specificity of A28-A2. The determinants which are the product of the A2 allele in the antigen-presenting cell will match the determinants coded by the A2 allele in the recipient's cells (syngeneic). In addition, at least one allele coding for HLA specificities should also be unmatched (allogeneic) between the antigen presenting cell and the recipient. In this manner, both syngeneic and allogeneic determinants will be present at the surface of the antigen-presenting cell.

In a preferred embodiment of the invention, a suitable antigen-presenting cell is chosen wherein allogeneic determinants are predominantly expressed by the antigen-presenting cell. In this embodiment, most alleles coding for the various HLA specificities are unmatched between the antigen-presenting cell and the recipient. The phraseology "most alleles being unmatched at the various HLA specificities" and the like refer to unmatched alleles between donor antigen presenting cells and recipient individual in the range of from about 50% to less than 100%. Similarly, as used herein, the phraseology "allogeneic determinants are predominantly expressed by the antigen-presenting cell" and the like refer to the presence of allogeneic MHC class I or class II determinants in the range of from about 50% to less than 100%.

The semi-allogeneic immunogenic cells of the present invention may also be genetically selected by fusing an antigen presenting cell with a tumor cell such that the resulting hybrid cell express both syngeneic and allogeneic MHC determinants. According to such method, an antigen presenting cell is fused with a tumor cell via a cell fusion procedure.

According to the present invention, any antigen presenting cells as described hereinabove may be used for such cell fusion. Antigen presenting cells which are employed in cell fusion may express exclusively allogeneic MHC determinants, or may express predominantly allogeneic MHC determinants. The term "express exclusively allogeneic MHC determinants" refers to that the MHC determinants of the donor cells are completely unmatched with the MHC determinants of a recipient. The term "express predominantly allogeneic determinants" refers to the presence of allogeneic MHC class I or class II determinants in the range of from about 50% to less than 100%.

More preferably, the antigen presenting cells used for fusion are derivatives or mutant antigen presenting cells which may facilitate the selection of the resulting hybrid cells. For example, derivatives or mutant antigen presenting cells as those cells that require special nutrition supplements or have certain drug resistances. Many such derivatives or mutant antigen presenting cells are described and available in the art. For example, LM(TK−) cells, available from ATCC, are mutant fibroblast LM cells that are deficient in thymidine kinase. LM(TK−) cells die in growth medium containing HAT (hypoxanthine-aminopterin and thymidine). Those skilled in the art may appreciate many conventional procedures for obtaining such derivatives or mutant antigen presenting cells. For example, as described in the working examples, LM(TK−) cells may be cultured in growth medium containing ouabain for a period of time such that ouabain-resistant cells are enriched in the cell population.

Tumor cells which may be used for fusion express exclusively or predominantly syngeneic MHC determinants. The term "express exclusively syngeneic determinants" refers to that the MHC determinants expressed by the donor cells are the same (matched) as the MHC determinants expressed by the recipient. The term "express predominantly syngeneic determinants" refers to the presence of syngeneic MHC class I or class II determinants in the range of from about 50% to less than 100%. Such tumor cells include those cells from a tumor cell line, or more preferably, from a recipient's neoplastic cells. Various tumor cell lines are available to those skilled in the art, such as B16 melanoma cells, EO771 mammary adenocarcinoma cells, EL4 thymoma cells, and human melanoma cell lines, all of which may be obtained from American Type Culture Collection, Rockville, Md. (ATCC). In a preferred embodiment, the tumor cells used for fusion are from an animal, e.g. a mammal, afflicted with the tumor to be treated. Such tumors may be solid or hematological tumors, which include but are not limited to melanoma, lymphoma, plasmocytoma, sarcoma, glioma, thymoma, leukemias, breast cancer, prostate cancer, colon cancer, esophageal cancer, brain cancer, lung cancer, ovary cancer, cervical cancer, and hepatoma. Tumor cells may be obtained from the subject via routine clinical procedures.

Methods for cell fusion which may be employed in practicing the present invention are thoroughly described in the literature and include Polyethylene Glycol(or PEG) mediated-, Calcium phosphate mediated-, Lipofectin mediated- and electroporation mediated-cell fusions.

Semi-allogeneic hybrid cells resulting from a cell fusion procedure may be selected by well-known procedures, including selections based on drug resistance or special nutrition requirements as described herein above. For example, ouabain-resistant LM(TK−) cells are resistant to ouabain, but are sensitive to HAT. B16 cells are resistant to HAT, but are sensitive to ouabain. When LM(TK−) cells are fused with B16 cells, the resulting hybrid cells are resistant to both HAT and ouabain. Such hybrid cells may then be selected by growth medium containing both ouabain and HAT. Another example of the methods for selecting hybrid cells is fluorescence-activated cell sorting (FACS), a well-known procedure to those skilled in the art. See, e.g., Coligan et al. *Current Protocols in Immunology*, John Wiley & Sons Inc. (1994). In this method, certain surface molecules are recognized by specific antibodies which are fluorescently labeled. Cells which express these surface molecules may then be collected by a fluorescence activated cell sorter. Accordingly, hybrid cells may be selected as those cells expressing surface molecules of both parental cells (i.e., conventional antigen presenting cells and tumor cells) are selected as hybrid cells at the end of a cell fusion procedure. Many surface molecules may be examined, e.g., B7.1, ICAM, MHC molecules, or tumor associated antigens, against which specific antibodies are available. Such hybrid cells are examined for their surface MHC determinants to ensure that both syngeneic determinants and allogeneic determinants are present at the cell surface. Those skilled in the art may use a number of well known methods for this examination; for example, immunofluorescent staining followed by cytometric measurments. See Coligan et al. Current Protocols in Immunology, John Wiley & Sons Inc. (1994).

Further in accordance with the present invention, the genetically selecteded immunogenic cells express, in addition to semi-allogeneic MHC determinants, at least one antigen recognized by T cells.

In one aspect of the invention, the antigen presenting cells are genetically transformed with nucleic acid molecules coding for at least one antigen recognized by T cells.

In one embodiment according to this aspect of the present invention, the nucleic acid molecules coding for at least one antigen recognized by T cells are known RNA or DNA sequences coding for at least one antigen recognized by T cells.

Coding sequences useful for practicing the present invention may comprise any of a myriad of known sequences or fragment of known sequences which encode antigens recognized by T cells. "Fragment" is meant segment of DNA having sufficient length to encode an antigenic peptide of at least about 8 amino acids.

The present invention contemplates coding sequences for a number of tumor associated antigens, which include but are not limited to (1) genes coding for TAAs which are recognized by cellular immune responses (mediated primarily by cytotoxic T cells) and/or by humoral immune responses (mediated primarily by T helper cells), such as members of MAGE gene family, BAGE, Tyrosinase, CEA, CO17-1A MART-1, gp100, MUC-1, TAG-72, CA 125, Decapeptide 810, P1A; (2) mutated proto-oncogenes such as $p21^{ras}$, P210 gene (a product of bcr/abl rearrangement), and HER-2/neu; (3) mutated tumor suppressor genes such as p53; (4) tumor associated viral antigens such as HPV E7. Genes for such TAAs are fully described in the art, e.g., Shawler et al. (1997). Some tumor associated antigens are expressed in certain types of tumors, others are associated with a variety of types of tumors. In accordance with the present invention, the skilled artisan may choose particular coding sequences according to the type of tumor to be treated.

Coding sequences for antigens of an infectious agent are also contemplated by the present invention. The semi-allogeneic immunogenic cells of the present invention are especially useful against viruses, many of which mutate and change their outer envelope thereby frustrating neutralization by antibodies. In addition, the subject semi-allogeneic immunogenic cells are also useful against pathogens which quickly enter a host's cells and hide from circulating cells of the immune system. Examples of such intracellular parasites against which the semi-allogeneic immunogenic cells of the present invention are useful include *Borrelia, Chlamydia, Plasmodium, Legionella pneumophila, Leishmania*, the trypanosome responsible for Chagas' and the like.

According to the present invention, a coding sequence for an antigen is placed in a vector which can replicate within a cell. The coding sequence is operably linked to a promoter which functions in cells of an animal such as a mammal, and is contained within the vector. The recombinant vector comprising the promoter and coding sequence is then introduced into the antigen-presenting cell. The introduction of DNA into antigen-presenting cells can be accomplished through various well known procedures such as by transfection of viral and retroviral vectors comprising the DNA, transduction into a cell of modified virus particles, and physical/chemical techniques such as calcium phosphate transfection, complex formation with polycations or lipids, electroporation, particle bombardment and microinjection into nuclei.

Preferably, a selectable marker and termination sequence is included in the recombinant vector. Polyadenylation signals may also be incorporated into the expression vector. Plasmid and viral vectors useful for practicing the present invention are well known in the art and are described in Sambrook et al. *A Laboratory Manual,* Cold Spring Harbor Laboratory, N.Y. (1989). Promoters, 3' termination sequences, polyadenylation signals and selectable marker genes which function in human cells are also well known in the art and discussed in Sambrook et al. (1989).

In another embodiment of the invention, the nucleic acid molecules coding for at least one antigen recognized by T cells are DNA or RNA isolated from an infectious agent, such as a bacterium or virus, or from tumor cells. Such DNA or RNA is isolated and mechanically sheared (or cut with one or more appropriate restriction enzymes in the case of DNA), in order to generate high molecular weight fragments. The high molecular weight fragments are then introduced into the subject antigen-presenting cell. Virus particles may also be directly introduced into the antigen-presenting cell by transduction.

In a more preferred embodiment, genomic DNA is isolated from tumor cells, either from a tumor cell line as described hereinabove, or more preferably, from an animal's small primary or metastatic neoplasms, for transfer into the antigen presenting cells.

Tumor cells taken from a subject may be used directly for isolating DNA without further culturing in vitro. The population of transfected cells, selected for their general, nonspecific, immune-augmenting properties, expresses the range of tumor associated antigens that characterize an animal's tumor, including antigens that may be present on only a small proportion of the malignant cells.

In this aspect of the invention, neoplastic cells from either diffuse neoplasms or from part of an animal's tumor, are obtained during surgery, by needle aspiration or other well-known methods. Examples of neoplastic disease amenable to the practice of the present invention include solid tumors and hematological tumors, e.g., melanoma, lymphoma, plasmocytoma, sarcoma, glioma, thymoma, leukemias, breast cancer, prostate cancer, colon cancer, esophageal cancer, brain cancer, lung cancer, ovary cancer, cervical cancer, and hepatoma. Genomic DNA is then isolated and purified from the cell or tumor sample using methods well known in the art including those set out in Sambrook et al., 1989 A Laboratory Manual, Cold Spring Harbor Laboratory, N.Y. Neoplastic cells and tumor samples may also be grown in culture using methods well known in the art in order to increase the amount of DNA available for isolation.

Isolated, purified genomic DNA isolated from a tumor or cell culture is then is preferably mechanically sheared or cut with an appropriate restriction enzyme to render high molecular weight DNA fragments of about 20-25 Kb. In a most preferred method, the DNA is mechanically sheared using a 23 or 25 gauge needle.

Genomic DNA may be introduced into the antigen presenting cells by any of a number of methods known in the art such as calcium-phosphate co-precipitation, electroporation, cationic liposome-mediated transfection or by any of a number of other well known methods for introducing DNA into cells. According to the present invention, genomic DNA is introduced along with a selectable marker such as a gene conferring resistance to hygromycin, neomycin or any other antibiotics. A procedure such as these is well-known in the art as co-transfection or co-transformation. See Sambrook et al. Such marker genes are usually contained in a plasmid. Plasmids such as these are well-known and are available to those skilled in the art. In the co-transformation procedure of the present invention, the amount of the plasmid is preferably less than the amount of the genomic DNA to facilitate the selection of tranformants. Preferably, the ratio of plasmid vs genomic is about 1:3 to about 1:20; more preferably, the ratio is about 1:10. After transformation, transformants (i.e., cells having received the genomic DNA and the marker gene) are selected as those cells growing in selection medium, e.g., medium containg antibiotics.

In another aspect of the invention with regard to the subject semi-allogeneic immunogenic cells expressing at least one antigen recognized by T cells, antigen presenting cells are genetically modified to express at least one antigen recognized by T cells via the cell fusion process as described hereinabove. Accordingly, antigen presenting cells are fused with tumor cells. The hybrid cells resulting from the fusion process express at least one T-cell recognizable antigen which is expressed by the parental tumor cells, preferably, a tumor associated antigen. The expression of at least one antigen on the hybrid cells may be confirmed by a number of well-known methods, such as immuno-fluorescent staining and cytometric measurements as described hereinabove. In this regime, transformation or transfection of nucleic acid molecules coding for tumor associated antigens is not necessary.

As discussed hereinabove, antigen presenting cells, which express MHC determinants that are semi-allogeneic to a recipient and also express at least one antigen recognized by T cells, are genetically selected via, e.g., transformation/transfection, HLA typing or cell fusion,.

In another aspect of the present invention, the antigen presenting cells employed in the present invention produce costimulatory molecules involved in T cell activation such as B7 and ICAM. For example, human fibroblasts are known to produce costimulatory molecules such as B7-1 and ICAM.

According to the present invention, the subject semi-allogeneic immunogenic cells do not require transformion and/or expression of a nucleic acid sequence coding for at least a cytokine. In a preferred embodiment of the present invention, the semi-allogeneic immunogenic cells may be engineered to express a coding sequence for at least one cytokine. In a preferred embodiment, the coding sequence is introduced into antigen-presenting cells prior to introducing high molecular weight DNA, or an expression vector with coding sequence for a particular antigen, or a cell fusion procedure. The introduction into the antigen-presenting cells of multiple coding sequences for different cytokines is also contemplated by the present invention. Examples of cytokines useful for practice of the present invention include interleukin-1, interleukin-2, interleukin-3, interleukin-4, interleukin-5, interleukin-6, interleukin-7, interleukin-8, interleukin-9, interleukin-10, interleukin-11, interleukin-12, interferon-α, interferon-γ, tumor necrosis factor, granulocyte macrophage colony stimulating factor, and granulocyte colony stimulating factor.

Coding sequence for one or more cytokines may be introduced into the semi-allogeneic antigen-presenting cell via an expression vector such as a plasmid or viral vector. Using vector construction methodologies well known in the art, coding sequence for at least one cytokine is operably linked to and under the control of a promoter which functions in human cells. For example, a plasmid based vector comprising the SV40 promoter may be used. Viral vectors made from the Moloney Murine Leukemia (MOMLV) virus, adeno-virus, Herpes-virus, pox-virus and Adeno-associated virus (AAV) are useful for expressing cytokine genes in the semi-allogeneic antigen-presenting cells of the present invention. Such vectors are well known in the art and available through the ATCC. In one embodiment of the invention, the vector is pZipNeoSVIL2 which comprises a gene for human IL-2 and a neo$^r$ gene, both under control of the Moloney Murine Leukemia virus long terminal repeat.

The present invention further provides a therapeutic composition comprising the semi-allogeneic immunogenic cells and a therapeutically acceptable carrier. As used herein, a therapeutically acceptable carrier includes any and all solvents, including water, dispersion media, culture from cell media, isotonic agents and the like that are non-toxic to the host. Preferably, it is an aqueous isotonic buffered solution with a pH of around 7.0. The use of such media and agents in therapeutic compositions is well known in the art. Except insofar as any conventional media or agent is incompatible with the semi-allogeneic immunogenic cells of the present invention, use of such conventional media or agent in the therapeutic compositions is contemplated. Supplementary active ingredients can also be incorporated into the compositions.

The therapeutic compositions of the present invention may be administered to an animal in need thereof. Accordingly, the present invention provides methods for inducing an immune response in an animal in need of such response, which comprise administering to an animal an immunologically effective amount of the subject semi-allogeneic immunogenic cells. The present invention also provides methods for preventing or treating a tumor in an animal, which comprise administering to an animal an anti-tumor effective amount of the subject semi-allogeneic immunogenic cells.

The term "animal" used herein encompasses all mammals, including human. Preferably, the animal of the present invention is a human subject.

The tumors contemplated by the present invention, against which the immune response is induced, or which is to be prevented or treated, may include and are not limited to melanoma, lymphoma, plasmocytoma, sarcoma, glioma, thymoma, leukemias, breast cancer, prostate cancer, colon cancer, esophageal cancer, brain cancer, lung cancer, ovary cancer, cervical cancer, hepatoma, and other neoplasms known in the art, such as those described by Shawler et al. (1997).

The immune response induced in the animal by administering the subject semi-allogeneic immunogens may include cellular immune responses mediated primarily by cytotoxic T cells, capable of killing tumor cells, as well as humoral immune repsonses mediated primarily by helper T cells, capable of activating B cells thus leading to antibody production. A variety of techniques may be used for analyzing the type of immune responses induced by the subject immunogenic cells, which are well described in the art; e.g., Coligan et al. *Current Protocols in Immunolgy*, John Wiley & Sons Inc. (1994).

The term "preventing a tumor" used herein means the occurrence of the tumor is prevented or the onset of the tumor is significantly delayed. The term "treating a tumor" used herein means that the tumor growth is significantly inhibited, which is reflected by, e.g., the tumor volume. Tumor volume may be determined by various known procedures, e.g., obtaining two dimensional measurements with a dial caliper.

When "an immunologically effective amount", "an anti-tumor effective amount", or "an tumor-inhibiting effective amount" is indicated, the precise amount of the semi-allogeneic immunogenic cells to be administered can be determined by a physician with consideration of individual differences in age, weight, tumor size, extent of infection or metastasis, and condition of the patient. It can generally be stated that a therapeutic composition comprising the subject semi-allogeneic immunogenic cells should be preferably administered in an amount of at least about $1\times10^3$ to about $5\times10^9$ cells per dose.

The administration of the subject therapeutic compositions may be carried out in any convenient manner, including by aerosol inhalation, injection, ingestion, transfusion, implantation or transplantation. Preferably, the semi-allogeneic immunogens of the present invention are administered to a patient by subcutaneous (s.c.), intraperitoneal (i.p.), intra-arterial (i.a.), or intravenous (i.v.) injection. The therapeutically acceptable carrier should be sterilized by techniques known to those skilled in the art.

The teachings of the publications cited throughout the present specification are herein incorporated by reference.

The invention is further illustrated by the following specific examples which are not intended in any way to limit the scope of the invention.

EXAMPLE 1

Experimental Materials

Experimental Animals

Six to 8 week old specific pathogen-free C57BL/6J mice ($H-2^b$) and C3H/HeJ mice ($H-2^k$) were obtained from the Jackson Laboratory (Bar Harbor, Me.). They were maintained in the animal care facilities of the University of Illinois at Chicago according to NIH Guidelines for the Care and Use of Laboratory Animals. The mice were fed Purina mouse chow and water ad libitum. They were 8 to 12 weeks old when used in the experiments.

Cell Lines

Tumor cells used in the examples were obtained and maintained as follows. B16 cells, a highly malignant melanoma cell line derived from a spontaneous neoplasm occurring in a C57BL/6 mouse, were obtained from I. Fidler, (M. D. Anderson Cancer Center, Houston, Tex.). The cells were maintained by serial passage in histocompatible C57BL/6J mice, or at 37° C. in a humidified 7% $CO_2$/air atmosphere in growth medium. C1498 cells, a spontaneously occurring lymphoma cell line of C57BL/6 mouse origin, were obtained from the American Type Culture Collection (Rockville, MD). E1-4 thymoma cells and G1 261 glioma cells were also obtained from the American Type Culture Collection (Rockville, Md.). C1498 cells, E1-4 thymoma cells and G1 261 glioma cells were maintained at 37° C. in a humidified 7% $CO_2$/air atmosphere in growth medium. EO771 cells, a mammary adenocarcinoma cell line derived from a C57BL/6 mouse, were from the Tumor Repository of the Division of Cancer Treatment, Diagnosis and Centers of the National Cancer Institute (Frederick, Md.). EO771 cells were maintained by serial passage in compatible C57BL/6J mice. SB-1 cells were obtained from a spontaneous breast neoplasm arising in a C3H/HeJ mouse maintained in the animal facility at the University of Illinois at Chicago.

The antigen presenting cells used in the examples were obtained and maintained as follows. LM cells, a fibroblast cell line derived from a C3H/HeJ mouse ($H-2^k$), were obtained from the American Type Culture Collection (Rockville, Md.). LM cells were maintained at 37° C. in a humidified 7% $CO_2$/air atmosphere in growth medium. LM(TK−) cells, a thymidine-kinase-deficient fibroblast cell line of a C3H/He mouse ($H-2^k$) origin, were obtained from the American Type Culture Collection (Rockville, Md.). LM(TK−) cells were maintained at 37° C. in a humidified 7% $CO_2$/air mixture in growth medium. Because LM(TK−) cells were deficient in the enzyme thymidine kinase, they died within 14 days in growth medium containing 100 μM hypoxanthine, 0.4 μM aminopterin and 16 μM thymidine (HAT).

WR19M.1 cells, a mouse monocyte/macrophage cell line, were obtained from the American Type Culture Collection (Rockville, Md.), and were maintained at 37° C. in a humidified 7% $CO_2$/air atmosphere in growth medium Antisera.

An antiserum reactive with B16 melanoma cells was raised in C57BL/6J mice injected intraperitoneally (i.p.) with killed (by three rounds of freezing and thawing) B16 cells suspended in Freund's complete adjuvant (Spex Industries, Inc., Metuchen, N.J.). The antiserum reacted with B16 cells, but not with a variety of organs and tissues from C57BL/6J mice, or with a panel of various neoplastic cell lines (11). $H-2K^b$ (clone AF6-88.5 of BALB/c origin, IgG2a) and $H-2K^k$ (clone 25-9-3 of C3H origin, IgM) monoclonal antibodies (mAbs) were from Pharmingen, (San Diego, Calif.). Fluoroscein isothiocyanate (FITC)-conjugated goat anti-mouse IgG was from Sigma, (St. Louis, Mo.). Anti L3T4 (CD4) mAbs were from Pharmingen (San Diego, Calif.); Lyt-2.2 (CD8) (hybridoma 3.155) mAbs were from M. Mokyr, (University of Illinois, Chicago, Ill.) and anti-asialo GM1 mAbs were from Wako Chemical Co. (Dallas, Tex.). FITC labeled B7.1 mAbs were obtained from Pharmingen.

EXAMPLE 2

Modification of LM Cells for the Secretion of IL-2

LM cells ($H-2^k$), a fibroblast cell-line of C3H/HeJ mouse origin, were modified for IL-2-secretion by transduction of the replication-defective retroviral vector, pZipNeoSVIL-2, using techniques described previously in Sugden et al. (1985) *Mol. Cell. Biol.* 5: 410-413. The vector pZipNeoSVIL-2 was obtained from M. K. L. Collins, Institute of Cancer Research, London, England. The vector, packaged in GP+env AM12 cells, (from A. Bank, Columbia University, New York, N.Y.) included a gene for human IL-2 and a neor gene, both under control of the Moloney leukemia virus long terminal repeat. For use as a control, LM cells were transduced with the retroviral vector pzipNeoSV(X) (from M. K. L. Collins), also packaged in GP+env AM12 cells (LM-ZipNeo cells). pzipNeoSV(X) specified the neor gene, but lacked the gene for IL-2.

Virus-containing supernatants of GP+env AM12 cells transfected with pZipNeoSVIL-2 or pzipNeoSV(X) were added to LM cells, followed by overnight incubation at 37° C. in growth medium to which polybrene (Sigma; 5 µg/ml, final concentration) had been added. The growth medium consisted of Dulbecro's modified eagle's medium (DMEM) supplemented with 10% fetal bovine serum (FBS) and antibiotics. The cells were maintained for 14 days in growth medium containing 400 µg/ml of the neomycin analog, G418. The growth medium consisted of Dulbecco's modified Eagle's medium (DMEM) supplemented with 10% fetal bovine serum (FBS). One hundred percent of nontransduced LM cells died in the medium supplemented with G418 within this period. After selection, the surviving colonies were pooled and assayed for IL-2-secretion.

IL-2 secretion was detected by the capacity of the cell culture supernatants to sustain the growth of CTLL-2 cells, an IL-2-dependent cell line (from A. Finneagan, Rush Medical College, Chicago, Ill.), Bakker et al. (1994) *J. Exp. Med.* 179:1005-1009. Varying dilutions of the filtered culture supernatants (0.2 µm nitrocellulose; Gelman, Ann Arbor, Mich.) were transferred to 96-well plates (Falcon) containing $5\times10^3$ CTLL-2 cells in a final volume of 200 µl of growth medium per well. After incubation for 16 hrs., 0.5 µCi $^3$H-thymidine (Amersham, Arlington Heights, Ill.) was added to each well for 6 additional hrs. A standard curve was generated by adding varying amounts of recombinant human IL-2 (Gibco BRL, Grand Island, N.Y.) to an equivalent number of CTLL-2 cells. Afterward, the cells were collected onto glass fiber filters (Whittaker M. A. Products, Walkerville, Md.) using a PhD multiple harvester (Microbiological Associates, Bethesda, Md.) and washed with ethanol (95%) Radioactivity in the insoluble fraction was measured in a liquid scintillation spectrometer (Parkard Instrument Co, Downers Grove, Ill.). One unit of IL-2 gave half maximal proliferation of CTLL-2 cells under these conditions. Every third transfer, the transduced cells (LM-IL-2 and LM-ZipNeo cells) were passaged in growth medium containing 400 µg/ml G418.

The results (Table II) indicate that $1\times10^6$ retrovirally transduced LM cells formed approximately 100 units IL-2 in 48 hrs. (LM-IL-2 cells). The culture supernatants of non transduced LM cells or LM cells transduced with the IL-2-negative vector, pZipNeoSV(X), (LM-ZipNeo cells) did not stimulate the proliferation of CTLL-2 cells. Equivalent quantities of IL-2 were detected in the culture supernatants of LM-IL-2, but not LMZipNeo cells for more than 6 months of continuous culture.

EXAMPLE 3

Modification of LM-IL-2 Cells for the Expression of $H-2K^b$ pBR327H-$2K^b$ (Biogen Research Corp., Cambridge, Mass.), a plasmid encoding MHC $H-2K^b$-determinants was used to modify LM cells (LM-IL-$2K^b$ cells). Ten µg of pBR327H-$2K^b$ and 1 µg of pBabePuro (M. K. L. Collins) a plasmid conferring resistance to puromycin were mixed with Lipofectin (Gibco BRL) according to the instructions of the supplier, and then added to $1\times10^6$ LM-IL-2 cells in 10 ml of Dulbecco's modified Eagle's medium (DMEM) without fetal bovine serum (FBS). The plasmid pBabePuro, Vile et al. (1993) *Cancer Res.* 53:962-967, was included to increase the likelihood that cells that were converted to resistance to puromycin had taken up pBR327H-2Kb. (The ratio of pBR327H-$2K^b$ to pBabePuro added to the cells was 10:1). For use as a control, an equivalent number of LM-IL-2 cells was transfected with 1 Mg of pBabePuro alone. The cells were incubated for 18 hrs. at 37° C. in a $CO_2$/air atmosphere, washed with DMEM, followed by the addition of growth medium. After incubation for 48 hrs., the cell cultures were divided and replated in growth medium supplemented with 3.0 µg/ml puromycin (Sigma) followed by incubation at 37° C. for 7 additional days. The surviving colonies were pooled and tested by staining with specific fluorescein conjugated antibodies for the expression of H-2Kb-determinants. One hundred percent of non-transfected LM-IL-2 cells maintained in growth medium containing puromycin died during the seven day period of incubation. LM-IL-2 cells transduced with the plasmid (pBR327H-$2K^b$ cells), or nontransduced LM-IL-2 cells, were dissociated from 100 MM2 tissue culture petri dishes with EDTA (0.1 mM) and then incubated for 1 hr. at 40 with FITC-conjugated anti-H-$2K^b$, anti-H-$2K^k$, or anti-H-$2D^b$ mAbs. As a control, aliquots of the cell suspensions were treated in the same way except that FITC-conjugated-$IgG_{2a}$, isotype serum was substituted for the mAbs. After three washes with PBS (pH 7.4), at least $1\times10^4$ cells of each type were analyzed for fluorescent staining in a flow cytofluorograph.

EXAMPLE 4

Immunofluorescent Staining and Cytofluorometric Measurments

Quantitative immunofluorescence measurements were used to detect the expression of $H-2K^b$-determinants by LM-IL-2 cells transfected with pBR327H-$2K^b$ (LM-IL-$2K^b$ cells). The measurements were performed in an Epic V flow cytofluorograph (Coulter Electronics, Hialeah, Fla.) equipped with a multiparameter data-acquisition and display system (MDADS). For the analysis, a single cell suspension was prepared from the monolayer cultures with 0.1 mM ethylene diamine tetra acetic acid (EDTA) in phosphate buffered saline (pH7.4) (PBS). The cells were washed with PBS containing 0.2% sodium azide and 0.5% FBS. Afterward, fluorescein isothiocyanate (FITC)—conjugated H-$2K^b$ monoclonal antibodies (mAbs) (clone AF6-88.5; Pharmingen, San Diego, Calif.) were added to the cells, followed by incubation at 4° C. for 1 hr. The cells were then washed with PBS containing 0.5% FBS and 0.2% sodium azide. One-parameter fluorescence histograms were generated by analyzing at least $1\times10^4$ cells. Background staining was determined by substituting cells stained with FITC-conjugated goat anti-mouse isotype $IgG_{2a}$ alone for cells stained with the specific antibodies. The 15 percent of cells that stained with the highest intensity were separated into plastic cell culture plates (Falcon) containing DMEM supplemented with 50% FBS. Immediately afterward, the cells were centrifuged at low speed and resuspended in growth medium in plastic cell culture plates, followed by incubation at 37° in a humidified 7% $CO_2$/air atmosphere. As controls, aliquots of the cell-suspension, incubated with FITC-labeled $IgG_2a$ isotype serum, or with FITC-labeled mAbs for H-2K, or $H-2D^b$ determinants, were analyzed as well. The results (FIG. 1) indicated that the transfected cells ($LM-IL-2K^b$ cells) stained positively with $H-2K^b$ but not with $IgG_{2a}$ isotype serum or $H-2D^b$ mAbs. As an additional control, the cells were analyzed in the same way for the expression of $H-2K^k$-determinants. As indicated (FIG. 1), LM-IL-2 cells, of C3H/He mouse origin, stained with $H-2K^k$ mAbs as well. The intensity of immunofluorescent staining of $Lm-IL-2K^b$ cells for $H-2K^b$-determinants was equivalent to that of spleen cells from naive C57BL/6J mice. The expression of $H-2K^b$-determinants was a stable property of the cells. Cells transfected with $pBR327h-2K^b$ stained with equivalent intensity with $H-2K^b$ mAbs after three months of continuous culture.

EXAMPLE 5

Transfection of $LM-IL-2K^b$ Cells with Genomic DNA from B16 Melanoma Cells

High molecular weight DNA isolated from B16 cells was used for the transfection of $LM-IL-2K^b$ cells, using the method described by Wigler et al., (1978) *Cell* 14: 725-731, as modified by Kim et al. (1992) *Int. J. Cancer* 51: 283-289. The DNA was first sheared by passage through a number 25 gauge needle. The molecular size of DNA at this point was greater than 23 kb, as determined by electrophoreses in 0.6% agarose gels. Afterwards, 100 ug of the sheared DNA was mixed with 10 μg pHyg (from L. Lau, University of Illinois, Chicago, Ill.), a plasmid that encodes the *E. coli* enzyme hygromycin B phosphotransferase (Sugden et al. (1985) Mol. Cell. Biol 5:410-413), conferring resistance to hygromycin B. The ratio of DNA of B16 cells to pHyg was 10:1 to increase the likelihood that cells that took up the plasmid DNA also took up DNA from the melanoma cells as well. The sheared DNA and pHyg were then mixed with Lipofectin, according to the manufacturer's instructions. The DNA/Lipofectin mixture was added to a population of $1\times10^7$ LM-IL-2Kb cells that had been divided into ten 100 mm plastic cells culture plates 24 hrs previously. Immediately after adding the DNA/Lipofectin mixture to the cells, the growth medium was replaced with DMEM. In some instances, DNA from B16-cells was omitted and 1 ug of pHyg mixed with Lipofectin was added to an equivalent number of $LM-IL-2K^b$ cells. In both instances, the cells were maintained for 14 days in growth medium containing 500 ug/ml hygromycin B (Boehringer Mannheim, Indianapolis, Ind.). One hundred percent of non-transfected $LM-IL-2K^b$ cells maintained in the hygromycin-growth medium died within this period. The surviving colonies (more than $2\times10^4$ in each instance) of hygromycin-resistant $LM-IL-2K^b$ cells transfected with pHyg and DNA from the melanoma cells ($LM-IL-2K^b$/B16) or with pHyg alone (LM-IL-2Kb) were pooled and used to induce an immunogenic response in mice. In some instances, the cells were disrupted by homogenization and sonication before injection into mice. The amount of IL-2 formed by $LM-IL-2K^b$/B16 cells was equivalent to that formed by LM-IL-2 or $LM-IL-2K^b$ cells as determined by the capacity of the cell culture supernatant to sustain the growth of CTLL-2 cells (Table II).

EXAMPLE 6

Survival of C57BL/6J Mice Injected with B16 Melanoma Cells and $LM-IL-2K^b$ cells Transfected with Genomic DNA from B16 Cells B16 melanoma is a highly malignant neoplasm of C57BL/6 mice. The animals exhibited no apparent resistance to the growth of the melanoma cells. One hundred percent of mice injected subcutaneously (s.c.) with $5\times10^3$ B16 cells died from progressive tumor growth in approximately 38 days.

As a first means of determining the immunotherapeutic properties of $LM-IL-2K^b$/B16 cells ($LM-IL-2K^b$ cells transfected with genomic DNA from B16 cells) toward the growth of the melanoma, C57BL/6J mice were injected s.c. with a mixture of B16 cells and $LM-IL-2K^b$/B16 cells, followed by two subsequent injections at weekly intervals of $LM-IL-2K^b$/B16 cells alone.

Figure 2:
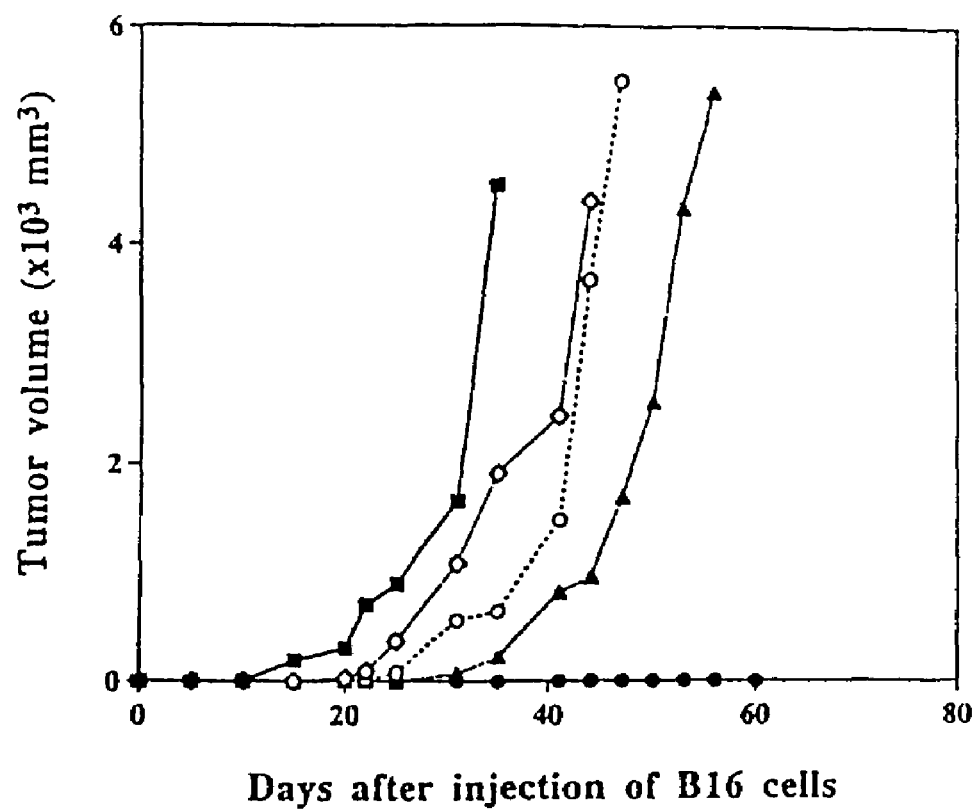
FIG. 2 graphically depicts tumor growth in C57BL/6J mice injected with a mixture of B16 melanoma cells and one of the following: media (solid squares), LMZipNeo cells (open diamonds), LM-IL-2(open circles), LM-IL-2/B16 cells (filled triangles); LM-IL-2Kb/B16 cells (filled circles).

Tumor growth was monitored in C57B1/6J mice injected with a mixture of B16 cells and $LM-IL-2K^b$/B16 cells (FIG. 2). C57BL/6J mice (5 per group) were injected s.c. with a mixture of $5\times10^3$ B16 cells and $2\times10^6$ $LM-IL-2K^b$/B16 cells. At the same time, the mice received a second injection i.p. of $2\times10^6$ LM-IL-2 Kb/B16 cells alone. As controls, the mice were injected according to the same protocol with equivalent numbers of B16 cells and LM-IL-2 cells, or with B16 cells and LM-IL-2/B16 cells. The mice were injected s.c. and i.p. twice more, at weekly intervals, with the same number of cells as in the initial injections, but without the additional B16 cells. Tumor volume was derived from two dimensional measurements obtained with a dial caliper. The results indicate that none of the mice injected with the mixture of B16 and $LM-IL-2K^b$/B16 cells developed tumors, while mice in various control groups all developed tumors within 15-60 days (FIG. 2).

Figure 3:
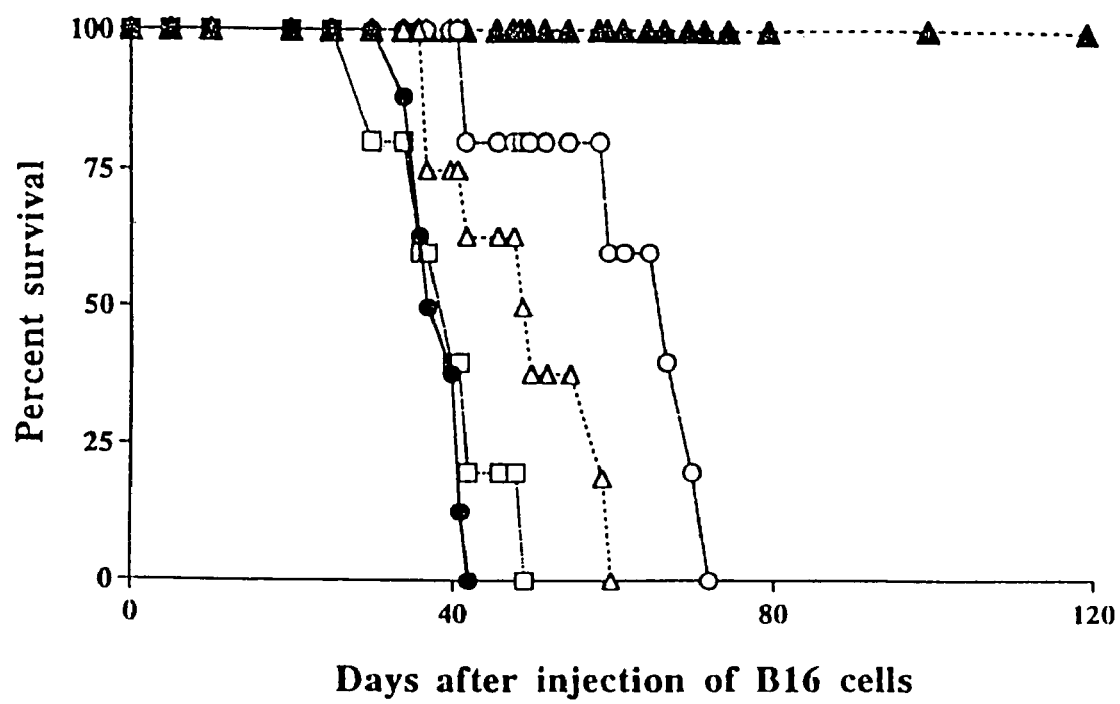
FIG. 3 graphically depicts survival of C57BL/6J mice injected with a mixture of B16 melanoma cells and one of the following: media (filled circles), LM ZipNeo cells (open squares), LM-IL-2 cells (open triangles), LM-IL-2/B16 (open circles), LM-IL-$2K^b$/B16 cells (filled triangles)

In a related experiment, the survival time of C57BL/6J mice injected with different combination of cell mixtures was measured (FIG. 3). C57BL/6J mice (5 per group) were injected s.c. with a mixture of $5\times10^3$ B16 cells and $2\times10^6$ $LM-IL-2K^b$/B16 cells. At the same time, the mice received a second injection i.p. of $2\times10^6$ LM-IL-2 $K^b$/B16 cells alone. As controls, other naive (untreated) C57BL/6J mice were injected according to the same protocol with equivalent number of B16 cells and LM-ZipNeo cells, with B16 cells and LM-IL-2 cells, with B16 cells and LM-IL-2/B16 cells or with B16 cells alone. The mice in each treatment group were injected twice more, at weekly intervals, with the same number of $LM-IL-2K^b$/B16, LM-ZipNeo cells, LM-IL-2 or LM-IL-2/B16 cells, but without additional B16 cells. Mean survival times were 38.4+2.8 days for mice injected with viable B16 cells alone; 39.4+7.1 days for mice injected with viable B16 cells and LM-Zip-Neo cells, 47.7+9.6 days for mice injected with viable B16 cells and LM-IL-2 cells; 62.2+12.2 days for mice injected with viable B16 cells and LM-IL-2/B16 cells; and >120 days for mice injected with viable B16 cells and $LM-IL-2K^b$/B16 cells. Mice injected with a mixture of B16 cells and non IL-2-secreting LM-ZipNeo cells, or with B16 cells alone, developed progressively growing neoplasms and died in approximately 40 days. Other naive C57BL/6J mice were injected with a mixture of B16 cells and LM-IL-2 cells. The difference in the period of survival of mice injected with B16 cells alone, and with the mixture of B16 cells and LM-IL-2 cells was not significant (P>0.1).

To determine the involvement of $H-2K^b$-determinants in the immunogenic properties of the cells, the survival of mice injected with B16 cells and LM-IL-2/B16 cells (LM-IL-2 cells transfected with DNA from B16 cells) was compared to the survival of mice injected with B16 cells and LM-IL-2K$^b$/B16 cells. The Student t test was used to determine the statistical differences between the survival and cytotoxic activities in mice in various experimental and control groups. A p value of less than 0.05 was considered significant. As shown by the data (FIG. 3), the survival of mice injected with the mixture of B16 cells and LM-IL-2/B16 cells was significantly less than the survival of mice injected with the mixture of B16 cells and LM-IL-2K$^b$/B16 cells (p<0.001)

Mice injected with a mixture of B16 cells and LM-IL-2K$^b$/B16 cells survived significantly longer than mice in various control groups. The animals exhibited long-term resistance to the growth of the melanoma. These results demonstrate that the greatest immunotherapeutic benefit was in the group of mice treated with immunogenic cells which expressed both syngeneic and allogeneic MHC determinants, which were transformed with the genomic DNA from the tumor, and which were also transformed to secret IL-2.

Figure 4:
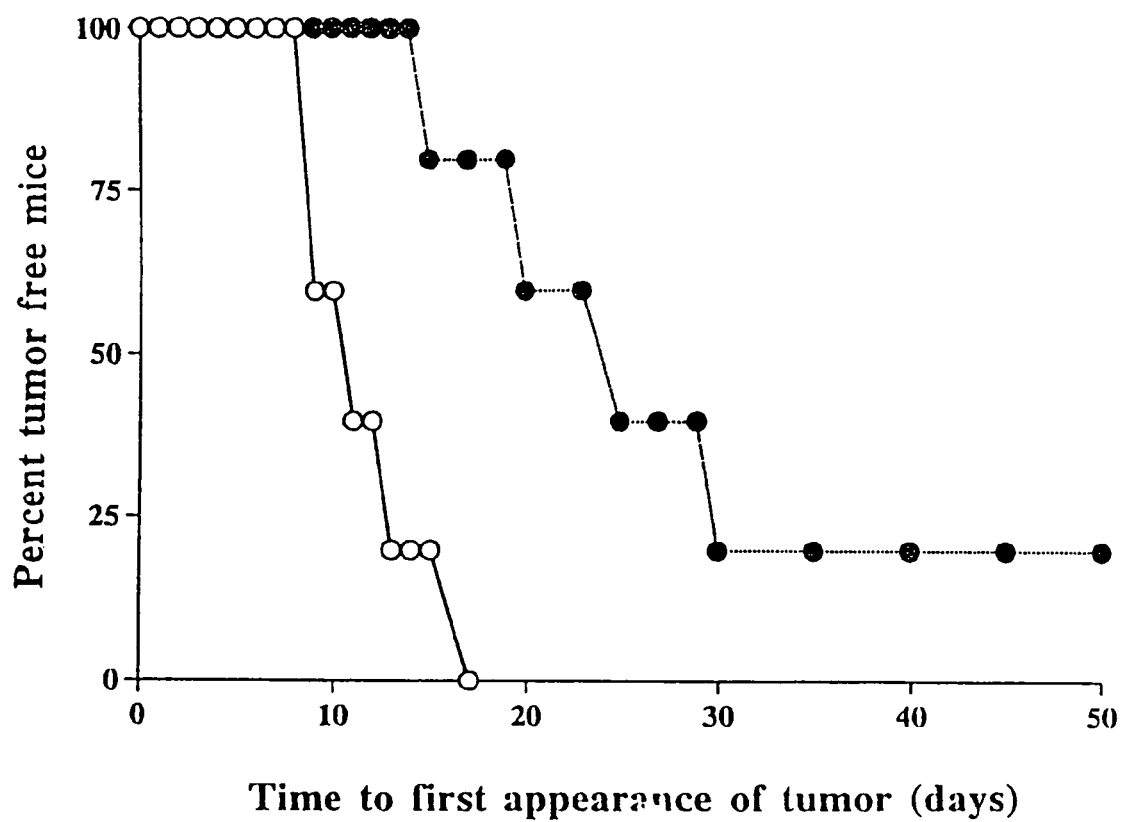
FIG. 4 graphically depicts the time to the first appearance of tumor in mice surviving after a prior injection of B16 cells and LM-IL-$2K^b$/B16 cells injected a second time with B16 cells alone. Open circles represent naive mice with a mean survival time (M.S.T.) of 34.4±2.2 days. Closed circles represent mice surviving 120 days and having a mean survival time of 53.0±7.1 days.

The long-term immunogenic properties of LM-IL-2K$^b$/B16 cells were investigated by injecting mice that survived the initial treatment with a second injection of B16 cells (FIG. 4). The second injection took place 150 days after the first injection of the mixture of B16 cells and LM-IL-2K$^b$/B16 cells. As a control, naive C57BL/6J mice were injected s.c. with an equivalent number of B16 cells. There were five mice in each group. As the data illustrate in FIG. 4, the first appearance of melanoma was significantly (P<0.001) delayed in mice treated previously with LM-IL-2K$^b$/B16 cells. Mean survival time (M.S.T.) of untreated mice was 34.4+2.2 days. M.S.T. of treated mice was 53.0+7.1 days (p<0.1).

EXAMPLE 7

Treatment of Mice Having Pre-Existent Melanoma with LM-IL-2K$^b$/B16 Cells

To determine if LM-IL-2K$^b$/B16 cells had a similar therapeutic effect on mice with established melanomas, C57BL/6J mice were injected s.c. with 5×10$^3$ B16 cells followed at varying times afterwards by, an injection s.c. and an injection i.p. of 2×10$^6$ LM-IL-2K$^b$/B16 cells at each injection site. An equivalent number of LM-IL-2K$^b$/B16 cells was injected s.c. and i.p. twice more at weekly intervals. As controls, other naive C57BL/6J mice were injected s.c. with a mixture or 5×10$^3$ B16 cells and 2×10$^6$ LM-IL-2K$^b$/B16 cells, and i.p. with 2×10$^6$ LM-IL-2 K$^b$/B16 cells, or s.c. with an equivalent number of B16 cells alone. There were 5 mice per group. Mean survival times were as follows: mice injected with B16 cells alone, 31.8+6.1 days; mice injected with a mixture of B16 cells and LM-IL-2K$^b$/B16 cells, 52.8+9.9 days; mice injected with LM-IL-2 K$^b$/B16 cells 5 days after the injection of B16 cells, 44.2+5.8 days; mice injected with LM-IL-2K$^b$/B16 cells 10 days after the injection of B16 cells, 39.3+3.6 days; mice injected with LM-IL-2 K$^b$/B16 cells 20 days after the injection of B16 cells, 34.4+4.0 days. P for survival of mice injected with the mixture of B16 cells and LM-IL-2 K$^b$/B16 cells vs. mice injected with B16 cells five days before LM-IL-2 K$^b$/B16 cells was less than 0.005; for mice injected with B16 cells ten days before the injection of LM-IL-2K$^b$/B16 cells, p was less than 0.04; for mice injected with B16 cells twenty days before the injection of LM-IL-2 K$^b$/B16 cells, p was less than 0.1.

Figure 5:
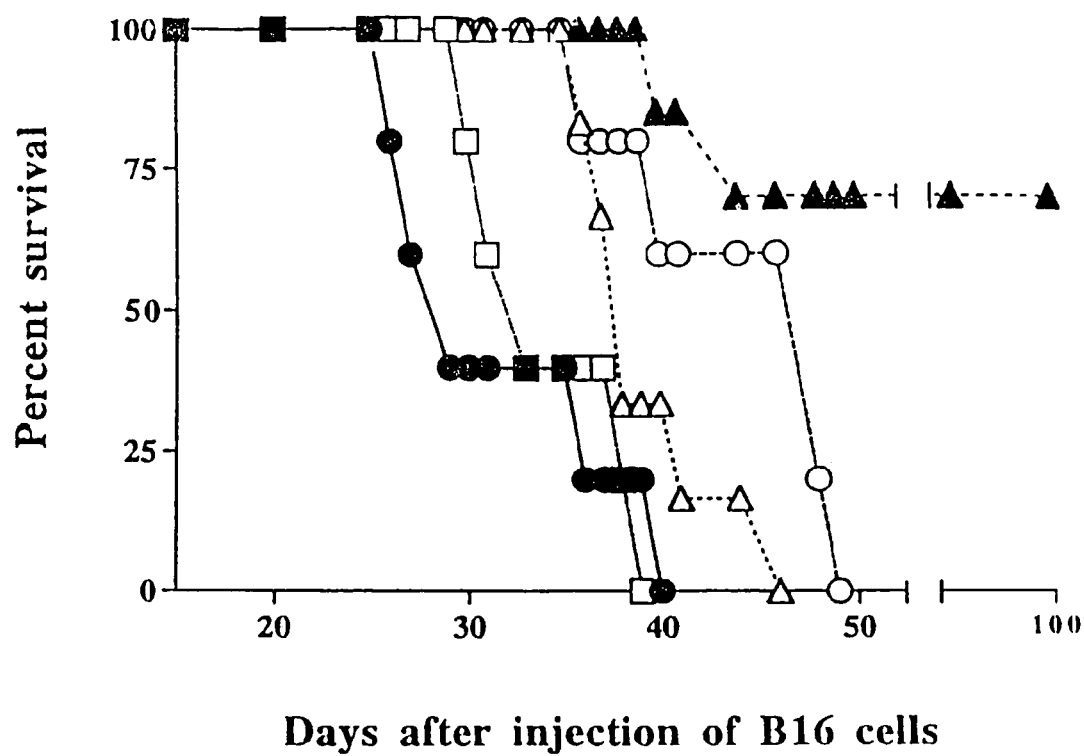
FIG. 5 graphically depicts survival of C57BL/6J mice with melanoma treated with LM-IL-$2K^b$/B16 cells. Closed circles represent mice injected with B16 cells alone. Open squares represent mice injected with B16 cells 20 days before LM-IL-$2K^b$/B16 cells. Open triangles represent mice injected with B16 cells 10 days before LM-IL-$2K^b$/B16 cells. Open circles represent mice injected with B16 cells 5 days before LM-IL-$2K^b$/B16 cells. Filled triangles represent mice injected with a mixture of B16 cells and LM-IL-$2K^b$/B16 cells.

As indicated (FIG. 5), mice injected with B16 cells five days, and ten days, before the first injection of LM-IL-2K$^b$/B16 cells survived significantly longer than mice injected with B16 cells alone (p<0.003 and <0.04 respectively). Mice injected with B16 cells 20 days before the first injection of LM-IL-2K$^b$/B16 cells failed to survive significantly longer than mice injected only with B16 cells (M.S.T.=34.4±4 and 31.8±6 days respectively; p=0.1).

EXAMPLE 8

Anti-Melanoma Cytotoxic Responses in C57BL/6J Mice Immunized with Disrupted LM-IL-2K$^b$/B16 Cells The experiments described above were carried out in mice immunized with viable LM-IL-2K$^b$/B16 cells. Spleen cell-mediated cytotoxicity experiments in mice immunized with homogenized/sonicated (disrupted) LM-IL-2K$^b$/B16 cells were carried out to determine if immunizations with disrupted cells would result in equivalent anti-melanoma cytotoxic responses. In the experiment, 4×10$^6$ LM-IL-2K$^b$/B16 cells suspended in 400 μl of growth medium were homogenized in a Takmar Tissue Mixer (Cincinnati, Ohio) for one minute at 4° C. followed by sonication for one minute at 4° in a Sonifier Cell Disrupter (VWR Scientific, Philadelphia, Pa.). Afterward, naive C57BL/6J mice were injected intraperitoneally (i.p.) and s.c. with 2×10$^6$ viable or an equivalent number (5×10$^6$) of disrupted LM-IL-2K$^b$/B16 cells at each injection site. The mice received two subsequent injections of the disrupted or viable cells at weekly intervals. Other naive C57BL/6J mice were injected according to the same protocol with viable LM-IL-2Kb or LM-IL-2 cells. One week after the last injection, the mice were killed and a standard $^{51}$Cr-release assay toward B16 cells was performed.

A pool of mononuclear cells from the spleens of 3 mice in each group were collected. A spleen cell-suspension was prepared by forcing the spleens though a number 40 gauge stainless steel screen in approximately 5 ml of ice-cold growth medium. The cells were transferred to 15 ml conical centrifuge tubes (Becton Dickinson, Franklin Lakes, N.J.), and large clumps of cells and cell debris were allowed to settle for 1 min. Afterward, cells remaining in the supernatant were collected, overlaid onto a Histopaque 1077 gradient (Sigma) and then centrifuged (400×g) for 30 min. at room temperature. The viability of the mononuclear cells collected from the gradients at this point was greater than 90%, as determined by trypan blue dye exclusion (0.4%). Aliquots of the cell-suspensions were co-incubated in growth medium at 37° C. for 5 days with mitomycin C-treated (Sigma Chemical Co., St. Louis, Mo.) (50 ug/ml for 45 min. at 37° C.) cells of the same type used to immunize the mice. The ratio of spleen cells to mitomycin-C-treated cells was 30:1. The incubation medium consisted of RPMI-1640 medium supplemented with 100 U/ml human IL-2, 10% FBS, 5×10$^{-2}$ mmol/L 2-β-mercaptoethanol, 15 mmol/L HEPES, 0.5 mmol/L sodium pyruvate and penicillin/streptomycin (Gibco). At the end of the 5 day incubation, the population that failed to adhere to the plastic cell culture flasks was collected and used as the source of effector cells for the cytotoxicity determinations.

For the $^{51}$Cr-release assay, 5×10$^6$ target cells were labeled with $^{51}$Cr during a 1 hr incubation at 37° C. in growth medium containing 100 uCi $^{51}$Cr (Amersham, Arlington Heights, Ill.). After three washes with DMEM, 1×10$^4$ of the $^{51}$Cr-labeled cells were incubated for 4 hrs. at 37° C. with the non plastic-adherent population of spleen cells from the immunized mice, at varying effective:target (E:T) ratios. Afterward, the percent specific cytolysis was calculated as:

$$\frac{\text{Experimental }^{51}Cr\text{ release} - \text{Spontaneous }^{51}Cr\text{ release}}{\text{Maximum }^{51}Cr\text{ release} - \text{Spontaneous }^{51}Cr\text{ release}} \times 100$$

Spontaneous release ranged from 10 to 15% of the maximal $^{51}$Cr release.

The Student t test was used to determine the statistical differences between the survival and cytotoxic activities in mice in various experimental and control groups. A p value of less than 0.05 was considered significant.

Figure 6:
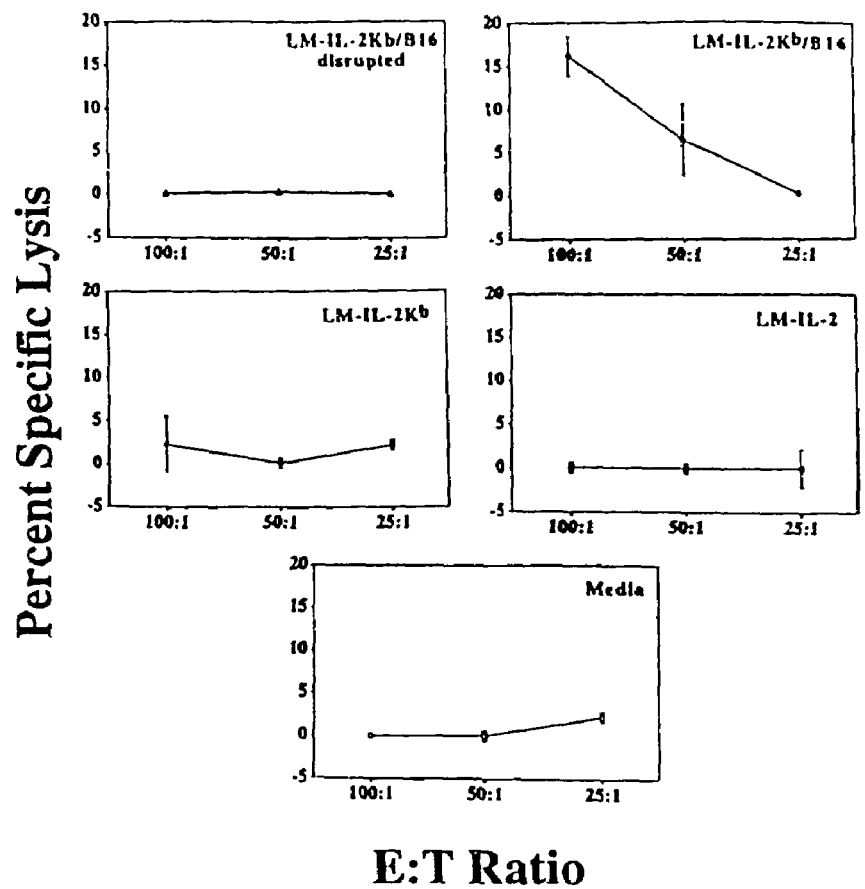
FIG. 6 graphically depicts cytotoxicity toward B16 cells in C57BL/6J mice injected with disrupted or intact LM-IL-$2K^b$/B16 cells.

As indicated (FIG. 6), cytotoxic reactions were present in the group of mice injected with the viable, but not the homogenized/sonicated cells. Spleen cells from mice injected with viable LM-IL-2K$^b$ or LM-IL-2 cells, like cells from naive mice, failed to exhibit cytotoxicity toward B16 cells.

EXAMPLE 9

Determination of the Classes of Effector Cells Activated for Anti-Melanoma Cytotoxicity in Mice Immunized with the Semi-Allopeneic Transfected Cells The effect of anti-Lyt-2.2 monoclonal antibodies (mAbs) (directed to Lyt-2.2$^+$ (CD8$^+$ T) cells) or anti-asialo G$_{m1}$ mAbs (directed to NK/LAK cells) on spleen cell-mediated cytotoxicity reactions was used to identify the predominant cell types activated for anti-melanoma cytotoxicity in mice immunized with the semi-allogeneic transfected cells described above.

C57BL/6J mice were injected with one of the following genetically modified cell-types: LM-ZipNeo, LM-IL-2, LM-IL-2/B16, LM-IL-2K$^b$ and LM-IL-2K$^b$/B16. As a control, one group of mice was injected with growth media. The mice received 2×10$^6$ cells s.c. and 2×10$^6$ cells i.p. Two additional injections at weekly intervals according to the same protocol were also administered to the mice. Seven days after the last injection, a pool of mononuclear cells from the spleens of 3 mice in each group were incubated for 5 days with mitomycin C-treated (50 ug/ml; 30 min) cells from the same type as first injected. After the five day period of incubation, the non-plastic-adherent cells were incubated at 4° C. for 1 hour with excess quantities of the mAbs [anti-Lyt-2.2$^+$ (CD8$^+$):hybridoma 3.155 (Sarmiento, et al. (1985) J. Immunol. 125:2665-2672) or anti-asialo G$_{M1}$ (Kasai et al. (1980) Eur. J. Immunol. 10:175-180 (Wako Chemical Co., Dallas, Tex.)] before the $^{51}$Cr-release assay was performed. The antibodies were titered such that the concentrations used were 5 times the amount required to saturate the binding of the specific cell-types from naive C57BL/6 mice, as determined by cytofluorometric analyses of serially diluted antibodies. At the end of the incubation, $^{51}$Cr-labeled B16 cells or $^{51}$Cr-labeled c1498 cells were added and the mixed cell cultures were incubated for 4 additional hours after which the specific release of isotope (% cytolysis) was determined. c1498 cells are an independently arising neoplasm of C57BL/6 mice. Table III reflects the results of the $^{51}$Cr-release assay. The values represent the mean ±SD of triplicate determinations.

As indicated in Table III, spleen cells from mice immunized with LM-IL-2K$^b$/B16 cells were cytotoxic for B16 cells and not c1498 cells.

As also indicated in Table III, the immune response was mediated primarily by CD8$^+$-CTLs. NK/LAK cells did not appear to be involved in the anti-melanoma cytotoxicity response.

EXAMPLE 10

Survival of C57BL/6J Mice Injected with a Mixture of B16 Melanoma Cells and Non-Cytokine-Secreting LMK$^b$/B16 Cells Non-IL-2-secreting LM mouse fibroblasts (H-2$^k$) were modified to express H-2K$^b$-determinants (LMK$^b$) by transduction with a plasmid (pBR327H-2K$^b$, Biogen Research Corp., Cambridge, Mass.), along with a plasmid (pBabePuro) conferring resistance to puromycin. The number of puromycin-resistant cells was expanded in vitro and then the expression of H-2K$^b$-determinants on such cells was tested by immunofluorescent staining essentially as described in Example 4.

After confirmation of the expression of H-2K$^b$-determinants, the LMK$^b$ cells were co-transfected with genomic DNA from B16 melanoma cells, along with a plasmid (pHyg) conferring resistance to hygromycin. Colonies of hygromycin-resistant, transfected cells (LMK$^b$/B16) (more than 5×10$^4$) were pooled, and the cell number was expanded in vitro. The cells were used without further modification in the experiment.

The immunotherapeutic properties of the genetically-modified cells were tested in C57BL/6J mice (H-2$^b$). The mice, which were between 8 and 12 weeks of age at the beginning of the experiment, were injected subcutaneously (s.c.) with a mixture of 5×10$^3$ B16 melanoma cells and 2×10$^6$ LMK$^b$/B16 cells. At the same time, the mice received a second intraperitoneal (i.p.) injection of 2×10$^6$ LMK$^b$/B16 alone. The mice received two subsequent s.c. and i.p. injections at weekly intervals of equivalent numbers of LMK$^b$/B16 cells, without additional B16 cells.

As controls, the mice received a s.c. injection of 5×10$^3$ B16 cells alone, or a s.c. injection of a mixture of 5×10$^3$ B16 cells and LM cells modified to express H-2Kb-determinants alone (LMK$^b$ cells) and a second i.p. injection of 2×10$^6$ LMK$^b$ cells alone. The mice in the group treated with LMK$^b$ cells received two subsequent s.c. and i.p. injections at weekly intervals of equivalent numbers of LMK$^b$ cells, without additional B16 cells.

There were eight mice in each group. P<0.001 for difference in survival of mice injected with B16 melanoma cells and LMK$^b$/B16 cells and mice injected with B16 cells alone, or mice injected with B16 cells and LMK$^b$ cells.

Figure 7:
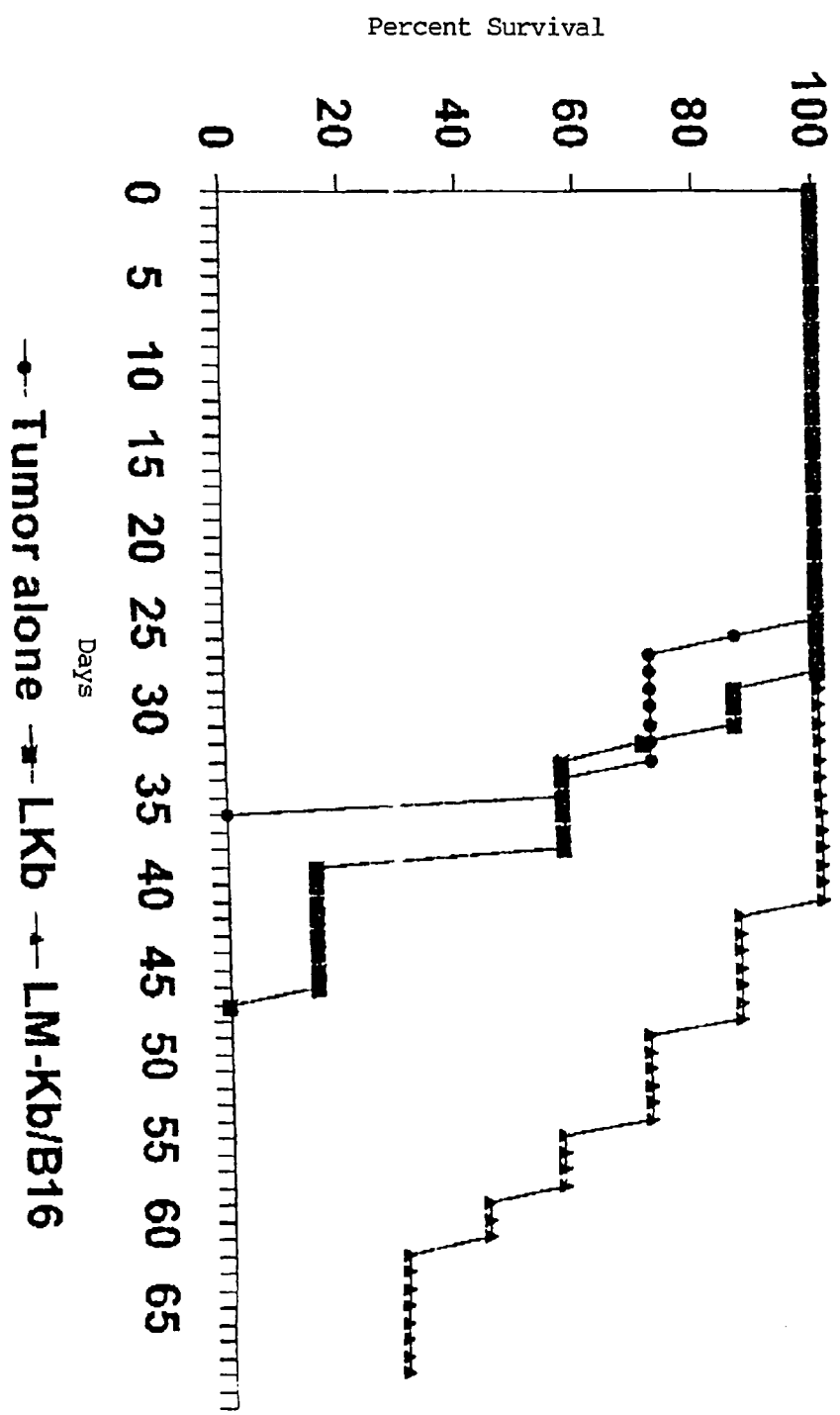
FIG. 7 graphically depicts survival of C57BL/6J mice injected with a mixture of B16 cells and non-cytokine-secreting cells. Filled circles represent mice injected with B16 cells; filled squares represent mice injected with B16 cells and LM-$K^b$ cells; filled triangles represent mice injected with B16 cells and LM-$K^b$/B16.

As indicated in FIG. 7, mice injected with a mixture of B16 cells and LMK$^b$/B16 cells survived significantly longer than mice injected with either B16 cells alone and mice injected with a mixture of B16 cells and LMK$^b$ cells. This result also indicates that a non-cytokine-secreting antigen presenting cell transfected with tumor genomic DNA also provides antitumor immunogenic effects.

EXAMPLE 11

Formation of B16 Melanoma X LM Fibroblast Hybrid Cells

B16 melanoma X LM fibroblast hybrid cells were prepared as follows. Ouabain-resistant LM(TK–) cells, a thymidine kinase-deficient variant, were first obtained by incubating approximately 10$^7$ cells for three weeks in growth medium containing 1 mM ouabain. The medium was changed at frequent intervals, no less than every third day, to remove dead, nonadherent cells. At the end of the incubation, colonies of LM(TK–) cells (approximately 5×10$^2$) proliferating in the ouabain-containing growth medium were recovered and pooled. The cells were maintained in growth medium containing 1 mM ouabain until use for the experiments. For fusion, $5\times10^6$ ouabain-resistant LM(TK−) cells were mixed with an equivalent number of B16 cells from in vitro culture and then incubated at 37° in growth medium containing PEG-1000, used to facilitate fusion. Twenty four hours afterward, the medium was replaced by growth medium containing both HAT and (1 mM) ouabain. LM(TK−cells were unable to grow in HAT-containing medium due to their lack of thymidine kinase, while unfused B16 cells were able to grow in such medium. LM(TK−) cells were selected to be ouabain-resistant, while B16 cells were sensitive to ouabain. Thus the hybrid cells, resulted from the fusion of LM(TK−) and B16 cells, complemented the properties of both types of parental cells and proliferated in a selection medium that contained both HAT and ouabain.

Figure 8:
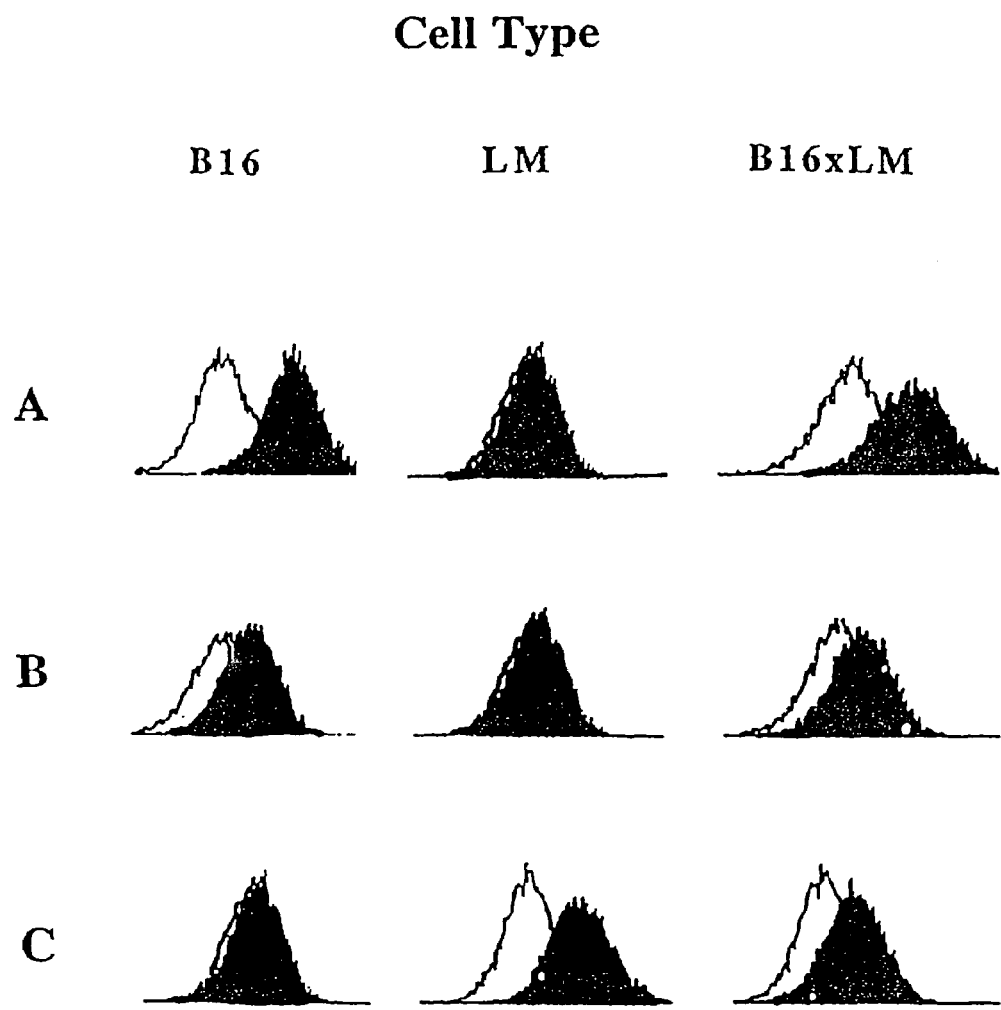
FIG. 8 depicts immunofluorescent staining of B16×LM hybrid cells. A cells incubated with anti-MAA antibodies. B cells incubated with anti-H-$2K^b$ mAb. C cells incubated with anti-H-$2K^b$ mAb. Black areas cells incubated with specific antibodies; white areas cells incubated with IgG2a isotype serum.

After fusion, B16 X LM hybrid cells were examined to ensure that they expressed MHC class I, determinants of both types of parental cells, $H-2^b$ determinants from the parental B16 cells and $H-2^k$ determinants from the parental LM(TK−) cells. Approximately $1\times10^3$ colonies of cells proliferating in HAT/ouabain medium were pooled and tested by quantitative immunofluorescent staining following basically the same protocol as described in Example 4. As indicated (FIG. 8) both the hybrid cells, and B16 cells, stained with anti $H-2K^b$ mAbs. LM cells failed to stain with anti $H-2K^b$ mabs. Under similar conditions, both the hybrid cells and LM cells stained with anti $H-2K^k$ mAbs. B16 cells failed to stain with anti $H-2K^k$ mAbs. The intensity of immunofluorescent staining of the respective cell-types was approximately the same. The results were consistent with the co-expression by the hybrid cells of both types of MHC class I-determinants of the parental cells.

A similar approach was used to detect the formation of (antibody-defined) MAAs by the hybrid, and parental cells. An antiserum raised in C57BL/6J mice injected with killed (by three rounds of freezing and thawing) B16 cells was used for this purpose (11). As indicated (FIG. 8), both B16 cells and the hybrid cells stained with the melanoma antibodies. LM cells failed to be stained with aliquots of the melanoma antiserum. As for MHC class I-determinants, the intensity of immunofluorescent staining of B16 cells and the hybrid cells with the melanoma antiserum was approximately the same. After six months of continuous culture, staining of the hybrid cells with the B16 antiserum and the anti $H-2K^b$ and anti $H-2K^k$ mAbs was equivalent to that found when the cells were first investigated.

Figure 9:
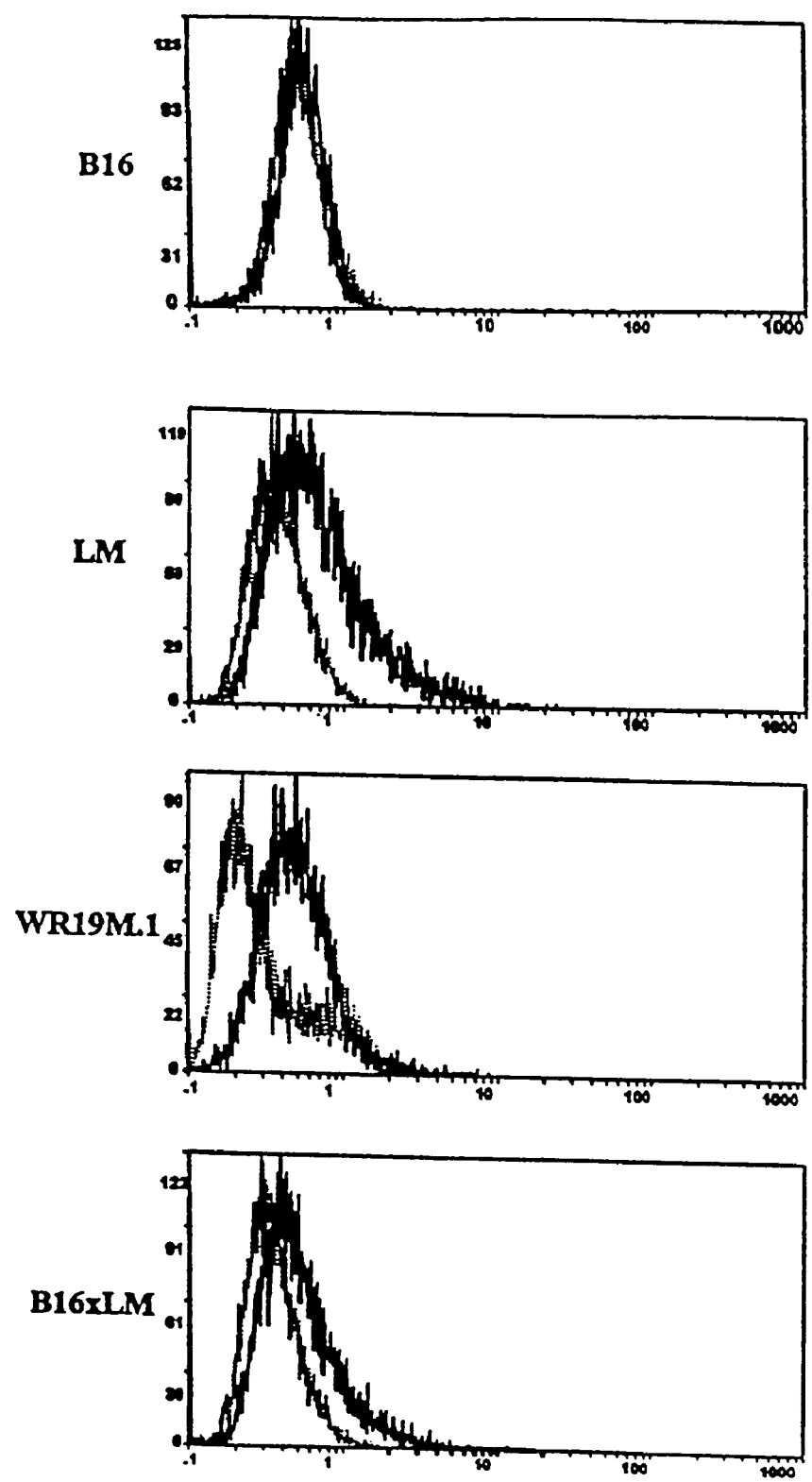
FIG. 9 depicts immunofluorescent staining of B16×LM hybrid cells with B7.1 mAb in a flow cytofluorograph. Fine lines represent cells incubated. with IgG2a isotype serum. Bold lines represent cells incubated with anti-B7.1 mAb.

In addition to testing for the expression of MAAs and MHC class I-determinants, the hybrid cells were investigated by immunofluorescent staining for the expression of B7.1, B7.2 and ICAM-1, co-stimulatory and adhesion molecules involved in the activation of cytotoxic T lymphocytes. The procedure for immunostaining was essential the same as described in Example 4. As indicated (FIG. 9), both the hybrid cells and LM cells stained positively with anti B7.1 mAbs (mean fluorescent intensities (MFI) of 23.2 and 19.2 above that of cells incubated with FITC-conjugated mouse $IgG_{2a}$ alone, taken as background). LM cells and the hybrid cells failed to stain positively for B7.2 or ICAM-1 (data not presented). B16 cells failed to stain for B7.1, B7.2 or ICAM-1 under these conditions (maximum MFI of 4.6 above background). WR19M.1 cells, a mouse monocyte/macrophage cell line, was included as a positive control. Like the hybrid cells and LM cells, the cells stained positively with anti B7.1 mAbs (MFI of 23.2 above background).

EXAMPLE 12

Figure 10:
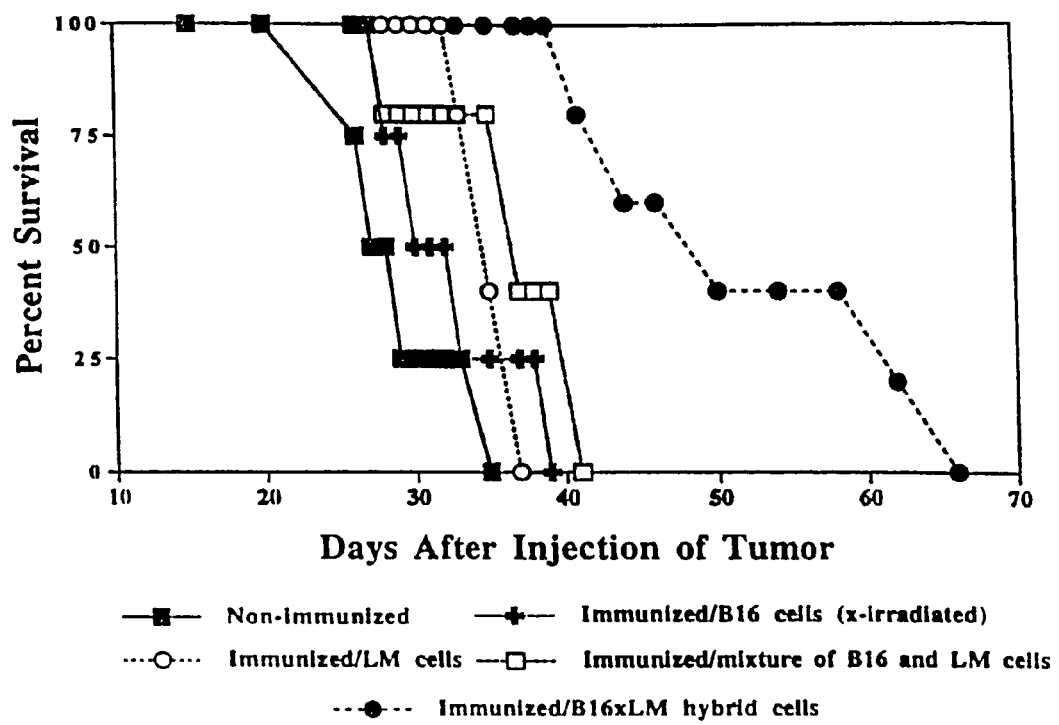
FIG. 10 depicts survival of C57BL/6J mice injected with a mixture of B16 cells and B16×LM hybrid cells. Mean survival time: (1) injected with viable B16 cells alone, 29.3±4.1 days (filled squares); (2) injected with viable B16 cells and irradiated B16 cells, 36.8±5.3 days (cross); (3) injected with viable B16 cells and LM(TK−) cells, 35.4±1.7 days (open circles); (4) injected with viable B16 cells, irradiated B16 cells and LM(TK−) cells, 36.8±5.3 days (open squares); and (5) injected with viable B16 cells and B16×LM hybrid cells, 52.6+11.0 days (filled circles). Survival of mice injected with viable B16 cells and B16×LM hybrid cells relative to survival of mice in any of the other groups, P<0.005.

Treatment with B16 X LM Hybrid Cells Prolonged the Survival of C57BL/6J Mice with Melanoma C57BL/6J mice exhibited no apparent resistance to the malignant proliferation of B16 melanoma cells. As few as $5\times10^3$ viable cells injected subcutaneously (s.c.) resulted in the death from progressive tumor growth of one hundred percent of the animals in less than 35 days. The effect of immunization with B16 X LM hybrid cells on the survival of C57BL/6J mice with B16 melanoma was determined by injecting naive mice s.c. with a mixture of $5\times10^3$ viable B16 cells and $1\times10^7$ hybrid cells. The mice received a single s.c. injection of $1\times10^7$ hybrid cells alone two weeks later. As a control, the mice received s.c. injections of an equivalent number of viable B16 cells, irradiated (5000 rads from a $^{60}$Co-source) B16 cells and LM(TK−) cells. The survival of mice in each group (six per group) was compared to the survival of mice injected s.c. with $5\times10^3$ viable B16 cells alone. As indicated (FIG. 10), mice injected with the mixture of B16 cells and the hybrid cells survived significantly longer ($P<0.005$) than mice injected with the mixture of B16 cells, irradiated B16 cells and LM(TK−) cells. The prolonged survival of mice injected with the hybrid cells, relative to the survival of mice injected with the mixture of B16 cells, irradiated B16 cells and LM(TK−) cells indicated that co-expression of both $H-2K^b$ and $K^k$ determinants by the same cell-type was required for an optimum immunotherapeutic result.

As additional controls, other naive C57BL/6J mice were injected according to the same protocol with a mixture of B16 cells and LM cells, with a mixture of B16 cells and irradiated B16 cells or with an equivalent number of B16 cells alone. As indicated (FIG. 10), the survival of mice in these groups was significantly less than that of mice in the group treated with the hybrid cells. The data indicated that the immunogenic properties of weak MAAs are enhanced if they were expressed by cells that formed both syngeneic and allogeneic determinants. This in vivo result was confirmed by examining the spleen cell-mediated cytotoxicity in vivo. The cytotoxicity of spleen cells obtained from C57BL/6J mice immunized with a mixture of (X-irradiated) B16 cells and LM(TK−) cells, or mice immunized with the hybrid cells was examined. The in vitro results were consistent with the in vivo results.

To investigate whether the hybrid cells retained the potential for growth in C57BL/6J mice, naive mice were injected s.c. with $10^7$ viable hybrid cells for each of three weekly injections. The mice exhibited no obvious ill effects. Tumors failed to form and the mice lived indefinitely (more than 6 months).

EXAMPLE 13

B16×LM Hybrid Cells Induced Immunity and Specific for Melanoma

To determine if mice injected with the hybrid cells developed immunity toward other types of neoplasms originating in C57BL/6 mice, the survival of naive C57BL/6J mice injected with a mixture of the hybrid cells and B16 cells was compared with the survival of mice injected with a mixture of the hybrid cells and G1 261 glioma, c1498 lymphoma cells or EL4 thymoma cells. The animals (five per group) received $5\times10^3$ of the respective tumor cells and $1\times10^7$ hybrid cells at the first injection, and $1\times10^7$ hybrid cells alone at weekly intervals on two subsequent occasions.

Figure 11:
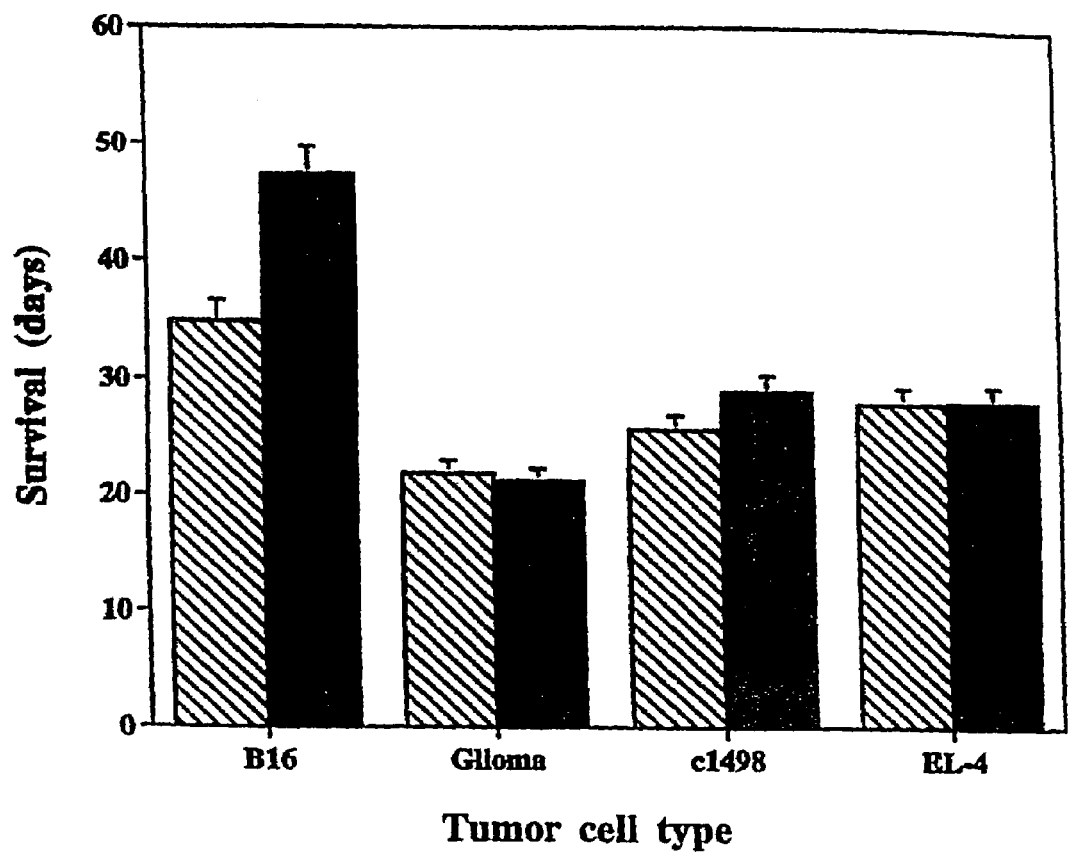
FIG. 11 depicts mean survival of C57B1/6J mice injected with a mixture of B16×LM hybrid cells and B16 melanoma, GL 261 glioma, c1498 lymphoma or EL-4 thymoma cells. Survival of mice injected with viable B16 cells and B16×LM hybrid cells relative to survival of mice in each of the other groups, P<0.005. Striped bars: mice injected with B16 melanoma, G1 261 glioma, c1498 lymphoma or EL-4 thymoma cells alone; solid bars: mice injected with a mixture of B16× LM hybrid cells and one of B16 melanoma, G1 261 glioma, c1498 lymphoma and EL-4 thymoma cells.

As indicated (FIG. 11), mice injected with the mixture of B16 cells and hybrid cells survived significantly (p<0.005) longer than mice in any of the other groups. With the exception of mice injected with B16 cells and the hybrid cells, mice in the control groups failed to survive longer than mice injected with an equivalent number of the respective tumor cells alone. The results were consistent with the expression of melanoma-specific, tumor associated antigens (TAAs) in a highly immunogenic form by the melanoma X fibroblast hybrid cells.

Figure 12:
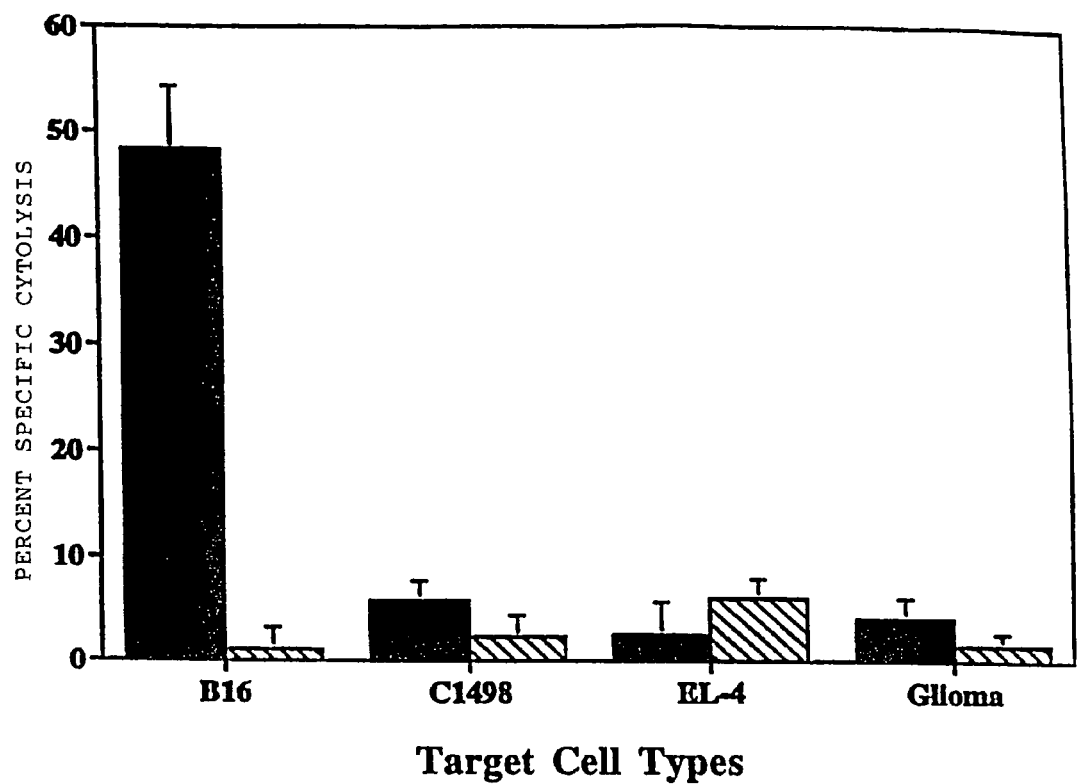
FIG. 12 depicts cytotoxic reactions (precent of specific cytolysis) toward B16 melanoma, c1498 lymphoma, EL-4 thymoma or G1 261 glioma cells in mice immunized with B16×LM hybrid cells. P<0.001 for specific cytolysis of B16 cells in the presence of spleen cells from mice injected with the hybrid cells relative to the specific cytolysis of c1498, EL-4 or G1 261 glioma cells. Solid bars: spleen cells from mice injected with B16×LM hybrid cells; striped bars: spleen cells from naive C57BL/6 mice.

Spleen cell-mediated cytotoxic reactions in mice injected with the hybrid cells were carried-out to determine if the specificity of the anti-melanoma immune-responses found in vivo was reflected by the results of studies performed in vitro. Naive C57BL/6J mice (two per group) were injected s.c. three times at weekly intervals with $1 \times 10^7$ viable hybrid cells. A spleen cell-suspension, prepared three weeks after the last injection, was tested for its reactivity toward $^{51}$Cr-labeled B16 cells, and, for comparison, against $^{51}$Cr-labeled c1498, EL-4 or G1 261 cells as well. The results (FIG. 12) indicated that the reactivity toward the melanoma cells was significantly (p<0.0005) higher than the reactions toward any of the other the other types of murine tumors tested. The reactivity toward c1498, EL-4 or G1 261 in mice immunized with the hybrid cells was not greater than that of naive mice.

EXAMPLE 14

CD8+(Lyt 2.2) Cells Were the Predominant Anti Melanoma Effector Cell-Type in Mice Immunized with B16 X LM Hybrid Cells The effect of mAbs for CD8$^+$(Lyt 2.2), CD4$^+$(L3T4) or asialo GM1-determinants on effector cells mediating the anti B16 melanoma response was used to determine the types of cells activated for anti melanoma immunity in mice immunized with the hybrid cells. Naive C57BL/6J mice (two per group) were injected s.c. with $1 \times 10^7$ hybrid cells for three weekly injections. One week after the last injection, the mice were killed and a spleen cell suspension was prepared. The cells were incubated in growth medium for 5 days additional days with mitomycin C-treated, (50 ug/ml; 30 min.; 37° C.) hybrid cells (ratio of hybrid cells: spleen cells 30:1). At the end of the incubation, the spleen cells were treated with excess quantities of CD4+, CD8+, and/or asialo GM1 mAbs for 1 hr. at 4° C. before a standard $^{51}$Cr release assay toward B16 cells was performed. The procedure is as described in Example 9.

Figure 13:
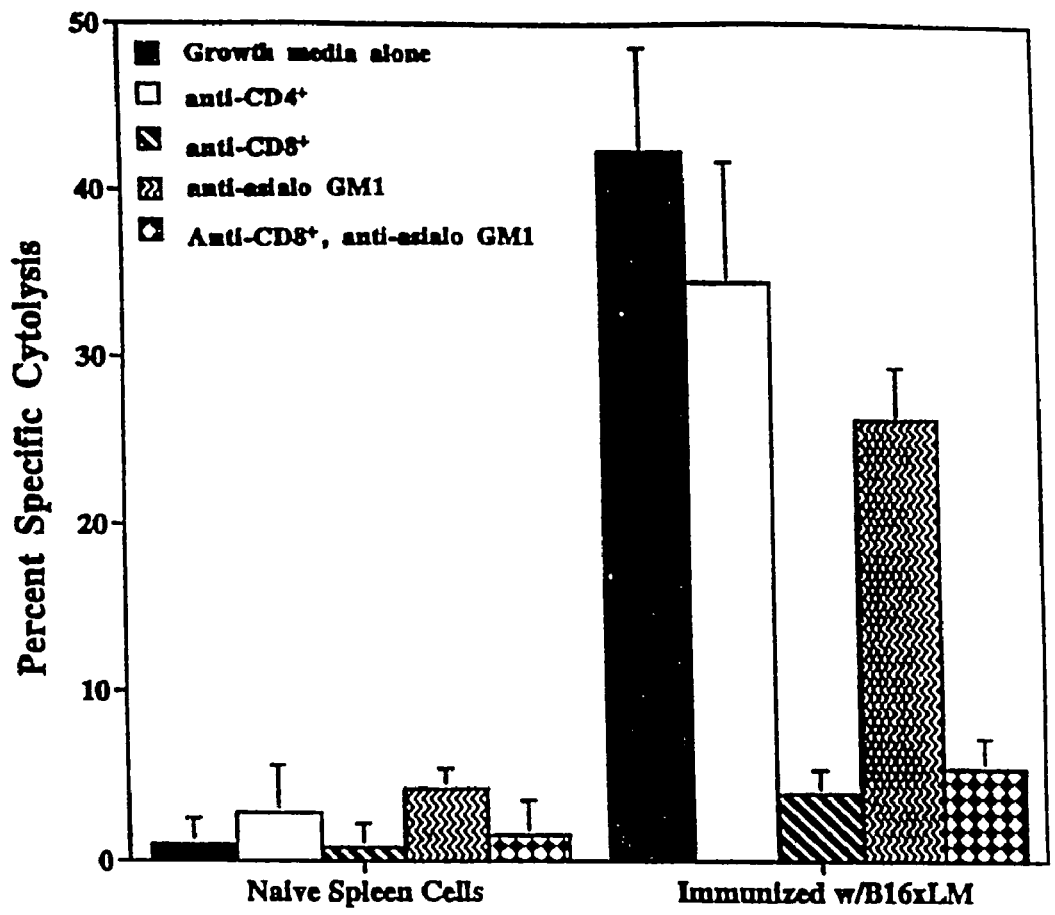
FIG. 13 depicts the effect of CD8+, CD4+ or asialo-GM1 mAb on spleen-cell mediated cytotoxic responses toward B16 cells in C57BL/6 mice immunized with B16×LM hybrid cells.

As indicated (FIG. 13), treatment of the cells with anti-CD8$^+$ mAbs or with a mixture of CD8$^+$ and asialo GM1 mAbs reduced the specific release of isotope to "background" (the anti melanoma activity present in a population of spleen cells from naive C57BL/6J mice) (p<0.005). Lesser inhibitory effects were detected in cell populations treated with CD4$^+$ or asialo GM1 mAbs alone. These results indicate that CD8+ cells are the predominant type of anti-melanoma effector cells in mice immunized with the B16xLM hybrid cells.

EXAMPLE 15

Survival of C57BL/6J Mice Injected with a Mixture of EO771 Breast Carcinoma Cells and LM-IL-2K$^b$ Cells Transfected With DNA From EO771 Cells (LM-IL-2K$^b$/EO771)

EO771 is a breast cancer cell line derived from a breast neoplasm that arose in a C57BL/6 mouse. The cells are maintained by serial transfer in syngeneic mice, or under standard cell culture conditions. C57BL/6J mice are highly susceptible to EO771 cells. One hundred percent of mice injected with $1 \times 10^3$ EO771 cells developed progressively growing neoplasms.

Figure 14:
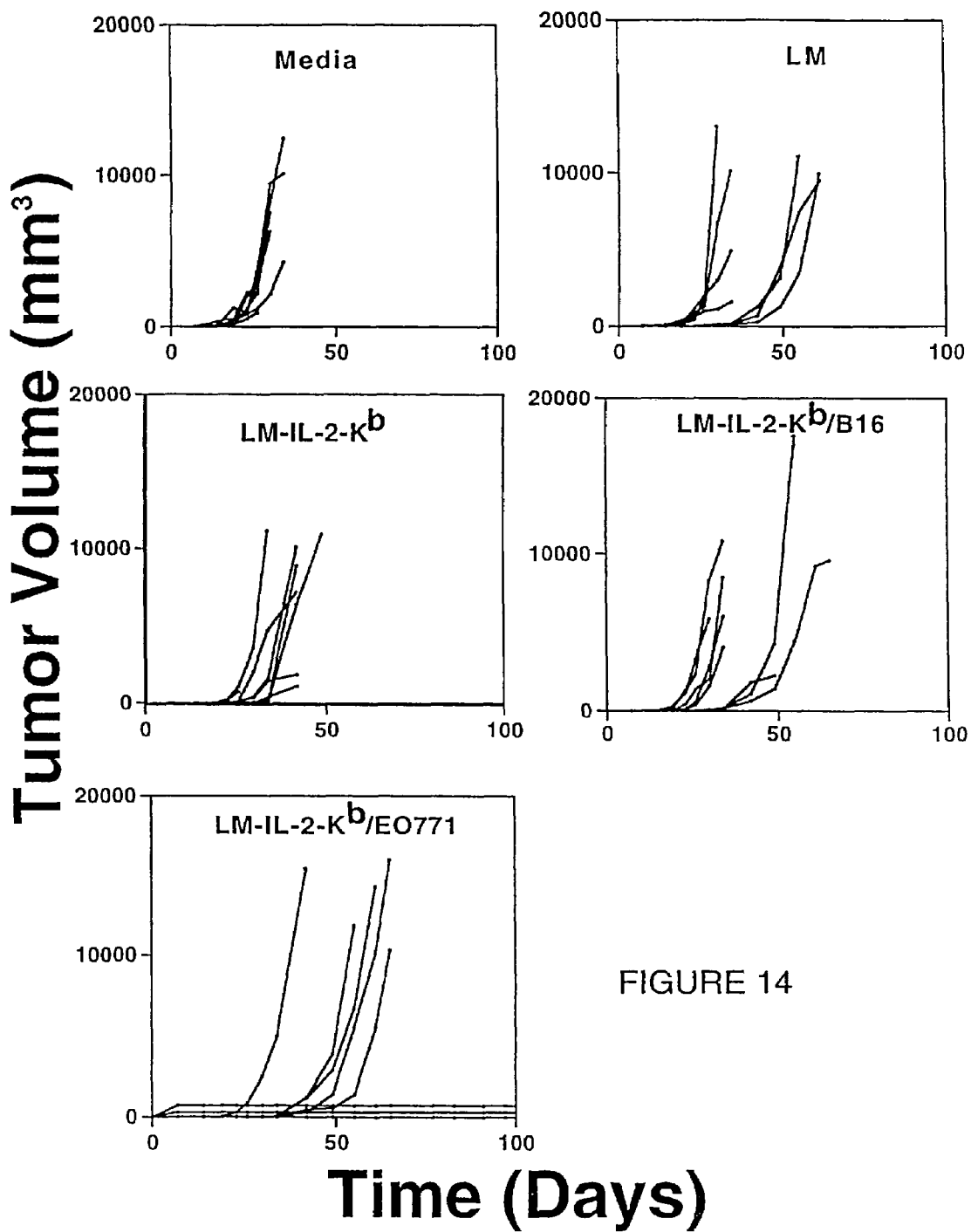
FIG. 14 depicts tumor growth in C57BL/6J mice injected with a mixture of EO771 breast cancer cells and LM-IL-$2K^b$/EO771 cells. Mean tumor volume was derived from two dimensional measurements obtained with a dial caliper. P<0.01 for the first appearance of tumor in the group of mice injected with EO771 cells and LM-IL-$2K^b$/EO771 cells and any of the other groups.

The potential immunotherapeutic properties of LM-IL-2K$^b$/EO771 cells against the growth of EO771 cells were determined in naive syngeneic C57BL/6J mice (FIG. 14). In the experiment, C57BL/6J mice (7 per group) were injected into the fat pad of the breast with a mixture of $5 \times 10^3$ EO771 cells and $2 \times 10^6$ LM-IL-2K$^b$/EO771 cells in a total volume of 200 µl. At the same time the mice also received an i.p. injection of $2 \times 10^6$ LM-IL-2K$^b$/EO771 cells alone, followed by two subsequent injections at weekly intervals of $2 > 10^6$ LM-IL-2K$^b$/EO771 cells i.p. and $2 \times 10^6$ LM-IL-2K$^b$/EO771 cells into the same breast as first injected, without additional EO771 cells. As a control, naive C57BL/6J mice were injected into the breast with an equivalent number of EO771 cells in growth media alone, followed by two subsequent injections at weekly intervals of growth media i.p. and growth media into the same breast as first injected. As additional controls, naive C57BL/6J mice were injected according to the same protocol with a mixture of EO771 cells and LM cells, with EO771 cells and non tumor-DNA transfected LM-IL-2K$^b$ cells, or with EO771 cells and LM-IL-2K$^b$ cells transfected with DNA from B16 cells (LM-IL-2K$^b$/B16). B16 is a melanoma cell line of C57BL/6J origin.

The results (FIG. 14) indicate that the first appearance of tumor was delayed in the group of mice injected with the mixture of EO771 cells and LM-IL-2K$^b$/EO771 cells, relative to that of mice in any of the other groups. Three mice in the group receiving EO771 cells and LM-IL-2K$^b$/EO771 cells failed to develop tumors. In those instances in which breast neoplasms appeared, the rate of tumor growth (two dimensional measurements) in each group was the same. These results indicated that specific partial immunity toward EO7771 cells developed in mice immunized with LM-IL-2K$^b$/EO771 cells.

Figure 15:
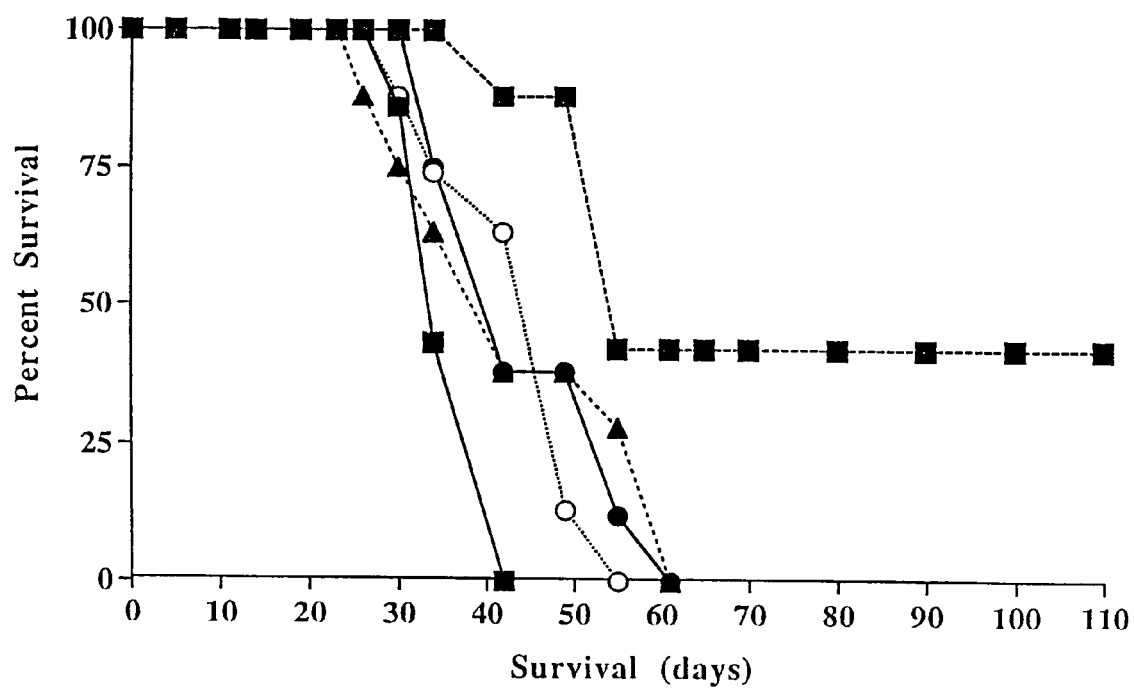
FIG. 15 depicts survival of C57BL/6J mice injected with a mixture of EO771 breast carcinoma cells and LM-IL-$2K^b$/EO771 cells. Mean survival times: Mice injected with viable EO771 cells alone, 34.5±5.8 days (filled squares); mice injected with viable EO771 cells and LM cells, 41±14 days (filled triangles); mice injected with viable EO771 cells and LM-IL-$2K^b$ cells, 44±9 days (open circles); mice injected with viable EO771 cells and LM-IL-$2K^b$/B16 cells, 46±11 days (filled circles); of the seven mice injected with viable EO771 cells and LM-IL-$2K^b$/EO771 cells>110 days (filled squares); and MST for remaining mice dying from progressive tumor growth=54±9. P for difference in survival of mice injected with viable EO771 cells and LM-IL-$2K^b$/EO771 cells relative to survival of mice in each of the other groups<0.001.

The development of partial immunity in C57BL/6J mice treated with LM-IL-2K$^b$/EO771 cells was emphasized by the finding that mice in the treatment group survived significantly (P<0.01) longer than mice in any of the various control groups, including mice injected with the mixture of EO771 cells and LM-IL-2K$^b$/EO771 cells (FIG. 15). In some instances, mice injected with the mixture of EO771 cells and LM-IL-2K$^b$/EO771 cells appeared to have rejected the breast cancer cells and survived indefinitely, more than 110 days. In addition, tumors failed to form in mice injected with semi-allogeneic LM-IL-2K$^b$/EO771 cells alone, or within the peritoneal cavities of mice injected into the breast with the mixture of EO771 cells and LM-IL-2K$^b$/EO771 cells.

Figure 16:
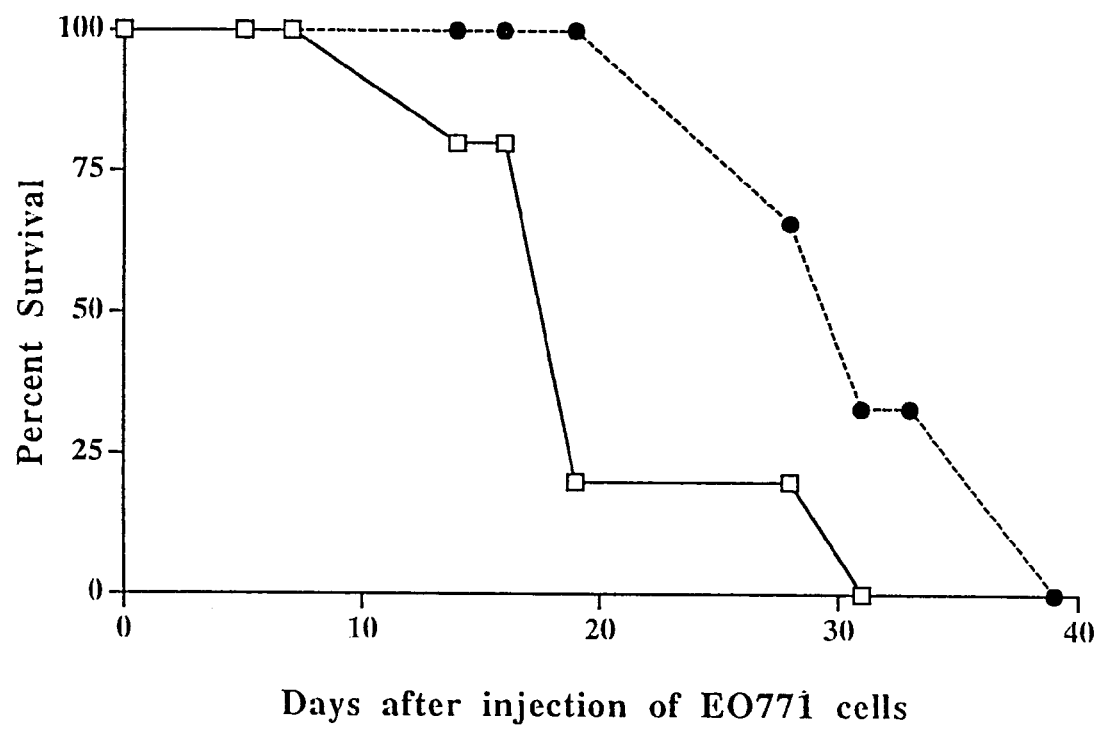
FIG. 16 depicts survival of C57BL/6J mice surviving a prior injection of EO771 cells and LM-IL-$2K^b$/EO771 cells injected with EO771 cells alone, with filled circles representing surviving mice injected with EO771 cells and open squares representing naive mice injected with EO771 cells.

To determine if surviving mice in the group injected with EO771 cells and LM-IL-2K$^b$/EO771 cells were resistant to a second injection of EO771 cells, the animals were injected into the fat pad of the breast with $5 \times 10^3$ EO771 cells alone 110 days after the first injection. The MST (33±6 days) of the surviving mice was significantly (P<0.02) greater than that of naive mice injected into the breast with an equivalent number of EO771 cells alone (20±6 days) (FIG. 16).

EXAMPLE 16

Survival of C3H/HeJ Mice Infected With a Mixture of Cells From a Spontaneous Adenocarcinoma of the Breast (SB-1) and LM-IL-2K$^b$ Cells Transfected With DNA From the Same Neoplasm (LM-IL-2K$^b$/SB-1)

Figure 17:
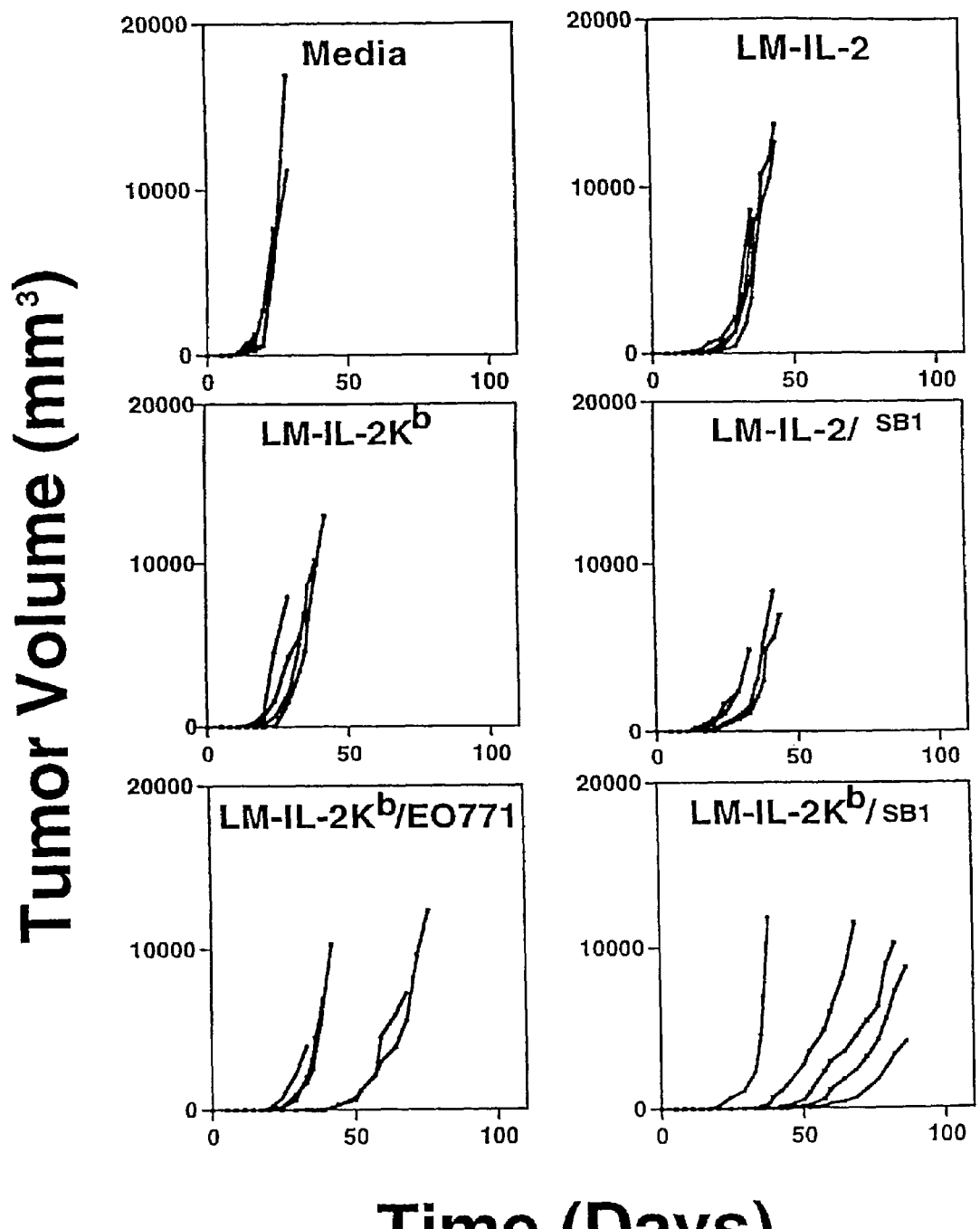
FIG. 17 depicts tumor growth in C3H/HeJ mice injected with a mixture of SB-1 breast cancer cells and LM-IL-$2K^b$/SB-1 cells. P<0.01 for the first appearance of tumor in the group of mice injected with SP1 cells and LM-IL-$2K^b$/SB-1 cells and any of the other groups.
Figure 18:
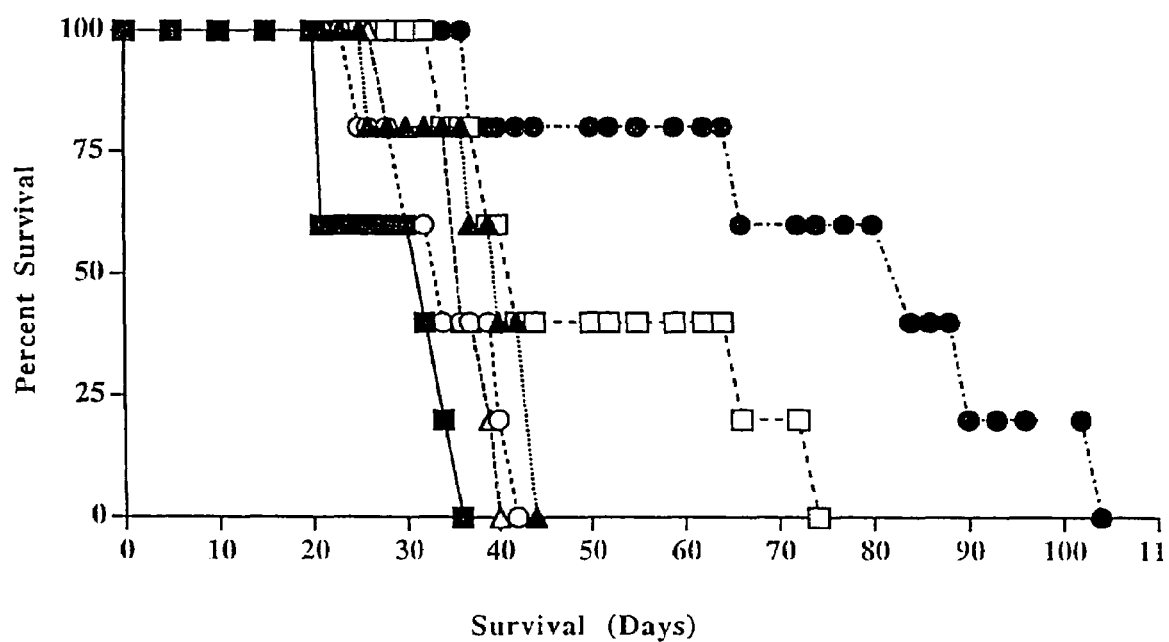
FIG. 18 depicts survival of C3H/HeJ mice injected with a mixture of SB-1 breast carcinoma cells and LM-IL-$2K^b$/SB-1 cells. Mean survival times: Mice injected with SB-1 cells alone, 29±7 days (filled squares); mice injected with SB-1 cells and LM-IL-2 cells, 38±8 days (filled triangles); mice injected with SB-1 cells and LM-IL-$2K^b$ cells, 34±7 days (open circles); mice injected with SB-1 cells and LM-IL-2/SB-1 cells, 36±5 days (open triangles); mice injected with SB-1 cells and LM-IL-$2K^b$/EO771 cells, 51+18 days (open squares); mice injected with SB-1 cells and LM-IL-$2K^b$/SB-1 cells, 76±26 days (filled circles). Survival of mice injected with SB-1 cells and LM-IL-2K$^b$/SB-1 cells relative to survival of mice in each of the other groups p<0.01.

The results of the prior experiments (Example 15) indicated that specific, partial immunity toward EO771 cells, a breast cancer cell line, was generated in C57BL/6J mice immunized with semi-allogeneic, IL-2-secreting mouse fibroblasts transfected with DNA from EO771 cells. Since the immunogenic properties of a breast cancer cell line might differ from those of a spontaneous breast neoplasm, the same protocol was followed to determine if an analogous response would be observed in C3H/HeJ mice immunized with semi-allogeneic, IL-2-secreting mouse fibroblasts transfected with DNA taken directly from a breast adenocarcinoma arising in a C3H/He mouse (SB-1 cells). Untreated C3H/HeJ mice exhibited no apparent resistance to the growth of SB-1 breast carcinoma cells. One hundred percent of mice injected into the breast fat pad with $1 \times 10^4$ SB-1 cells died from progressive tumor growth in approximately 30 days. The potential immunotherapeutic properties of LM-IL-2K$^b$/SB-1 cells were determined by injecting C3H/HeJ mice into the fat pad of the breast with a mixture of $1 \times 10^6$ SB-1 cells and $2 \times 10^6$ LM-IL-2K$^b$/SB-1 cells, and i.p. with $2 \times 10^6$ LM-IL-2K$^b$/SB-1 cells alone. The mice received two subsequent injections i.p. and two subsequent injections into the same breast as first injected with the same number of LM-IL-2K$^b$/SB-1 cells alone, as described previously. The time to the first appearance of tumor, rate of tumor growth and survival of mice injected with the mixture of SB-1 cells and LM-IL-2K$^b$/SB-1 cells was compared to the time to first appearance and survival of mice injected with SB-1 cells alone. There were five mice per group. The results (FIG. 17) indicated that the first appearance of a palpable tumor in the breasts of mice injected with the mixture of LM-IL-2K$^b$/SB-1 cells and SB-1 cells was delayed, relative to the first appearance of tumor in mice injected with SB-1 cells and growth media. Once the breast neoplasms first appeared, the rate of tumor growth (two dimensional measurements) in the treated and untreated groups was approximately the same. Consistent with the delayed appearance of tumor in the treated group, mice injected with the mixture of SB-1 cells and LM-IL-2K$^b$/SB-1 cells survived significantly (P<0.006) longer than mice injected with SB-1 cells alone (FIG. 18). In no instances were tumors detected at immunization sites injected with LM-IL-2K$^b$/SB-1 cells alone.

As additional controls, naive C3H/HeJ mice were injected according to the same protocol with a mixture of SB-1 cells and non transfected LM-IL-2 cells, with SB-1 cells and non transfected semi-allogeneic LM-IL-2K$^b$ cells, or with SB-1 cells and syngeneic LM-IL-2 cells transfected with DNA from SB-1 cells (LM-IL-2/SB-1). As indicated (FIGS. 17 and 18), with the exception of two mice in the group (5 per group) injected with the mixture of SB-1 cells and LM-IL-2K$^b$/EO771 cells, the first appearance of tumor, rate of tumor growth and survival of mice in each group was approximately the same as that of mice injected with SB-1 cells alone. The greatest immunotherapeutic benefit was in the group of mice injected with the mixture of SB-1 cells and LM-IL-2K$^b$ cells transfected with genomic DNA from SB-1 cells.

As an additional control, to determine the effect of immunizations with LM-IL-2K$^b$/EO771 cells on the growth of SB-1 cells, the independently arising breast neoplasm, naive C3H/HeJ mice were injected with a mixture of SB-1 cells and LM-IL-2K$^b$/EO771 cells. As indicated (FIG. 18), although mice injected with the mixture of SB-1 cells and LM-IL-2K$^b$/EO771 cells survived longer than mice injected with SB-1 cells alone, they died in significantly (P<0.01) shorter intervals than mice injected with SB-1 cells and LM-IL-2K$^b$ cells transfected with DNA from SB-1 cells.

EXAMPLE 17

Spleen Cell-Mediated Immune Responses Toward EO771 Cells Were Generated in C57BL/6J Mice Immunized With LM-IL-2K$^b$/EO771 Cells As described in Example 15, C57BL/6J mice injected with a mixture of EO771 cells and LM-IL-2K$^b$/EO771 cells survived significantly longer than mice in various control groups, including mice injected with a mixture of EO771 cells and LM-IL-2K$^b$ transfected with DNA from B16 melanoma cells. The results indicate that specific, partial immunity toward EO771 cells was generated in mice immunized with the semi-allogeneic, cytokine-secreting cells transfected with DNA from EO771 cells.

A standard $^{51}$Cr-release assay was used to characterize the anti-tumor immune response in mice injected with the mixture of EO771 cells and LM-IL-2K$^b$/EO771 cells. In the experiment, C57BL/6J mice were injected into the fat pad of the breast with a mixture of $5 \times 10^3$ EO771 cells and $2 \times 10^6$ LM-IL-2K$^b$/EO771 cells. At the same time the mice also received an injection i.p. of equivalent numbers of LM-IL-2K$^b$/EO771 cells alone, followed by two subsequent injections at weekly intervals of equivalent numbers of LM-IL-2K$^b$/EO771 cells i.p. and LM-IL-2K$^b$/EO771 cells into the same breast as first injected, without additional EO771 cells. The mice were sacrificed one week after the last injection of LM-IL-2K$^b$/EO771 cells. A pool of mononuclear cells from the spleens of 3 mice in each group were collected. A spleen cell-suspension was prepared and coincubated for five additional days with (mitomycin C-treated; 50 ug/ml; 30 min. at 370) LM-IL-2K$^b$/EO771 cells, after which a cytotoxicity determination toward $^{51}$Cr-labeled EO771 cells was performed. As controls, same protocol was followed except that spleen cells from mice injected with EO771 cells and LM cells, EO771 cells and LM-IL-2K$^b$ cells, or EO771 cells and LM-IL-2K$^b$/B16 cells were substituted for spleen cells from mice injected with EO771 cells and LM-IL-2K$^b$/EO771 cells. As an additional control, spleen cells were obtained from mice injected with EO771 cells alone.

The results (Table IV) indicate that the cytotoxic responses (specific $^{51}$Cr-release) toward EO771 cells in mice injected with the mixture of EO771 cells and LM-IL-2K$^b$/EO771 cells were significantly (P<0.01) higher than those in any of the other groups. The response toward EO771 cells in mice injected with the mixture of EO771 cells and LM-IL-2K$^b$ cells transfected with DNA from B16 melanoma cells was not significantly different than background (specific $^{51}$Cr-release from EO771 cells co-incubated with spleen cells from mice injected with EO771 cells alone). Immunizations with non-DNA-transfected LM-IL-2K$^b$ cells failed to generate cell mediated responses toward EO771 breast carcinoma cells in C57BL/6J mice.

As an additional control, to determine if cytotoxic responses toward LM cells were present in the spleen cell-suspensions that failed to react with EO771 cells, aliquots of the cell-suspensions from C57BL/6J mice injected with the different cell mixtures were tested for cytotoxic responses toward LM cells. As indicated (Table IV), the percent specific lysis was greater than fifty percent for cells from each group including cells from mice immunized with LM-IL-2K$^b$/B16 cells that failed to generate cytotoxic responses toward EO771 cells.

EXAMPLE 18

CD8+ Cells Infiltrated Breast Tumors Developing in Mice Infected With SB-1 and LM-IL-2K$^b$/SB-1 Cells and Mice Infected With EO771 and LM-IL-2K$^b$/EO771 Cells As described in Example 16, C3H/HeJ mice injected with a mixture of SB-1 cells and LM-IL-2K$^b$/SB-1 cells survived significantly longer than mice in various control groups.

Immunihistochemical staining was used to characterize the cellular infiltrate in breast tumors developing in mice injected with the mixture of SB-1 cells and LM-IL-2K$^b$/SB-1 cells. Primary antibodies for mouse CD4(L3T4), CD8a (Ly-2), CD11b or NK (Ly-49c) cells were used in the analysis. In these experiments, C3H/HeJ mice (3 mice per group) were injected into the fat pad of the breast with a mixture of $1\times10^6$ SB-1 cells and $2\times10^6$ LM-IL-2K$^b$/SB-1 cells, and i.p. with $1\times10^6$ LM-IL-2K$^b$/SB-1 cells alone. The mice received two subsequent i.p. injections and two subsequent injections into the same breast as first injected with equivalent numbers of LM-IL-2K$^b$/SB-1 cells alone, as described previously. One week after the last injection, the mice were sacrificed and breast neoplasms were quickly frozen in liquid nitrogen.

A representative tissue block was selected and 5-um frozen sections were prepared, mounted on clean glass slides and fixed with acetone. Afterwards, the sections were washed two times with 0.1 M PBS, placed in 3% $H_2O_2$ for 10 mins., and then washed three times with 0.1 M PBS. A 1:5 dilution of goat serum (Gibco BRL) in PBS (blocking buffer) was added to the slides (to reduce non-specific binding of primary antibodies) followed by incubation at 37° for 15 mins. After incubation, the slides were flooded with anti-mouse CD4 (L3T4), anti-mouse CD8a (Ly-2), anti-mouse CD11b (integrin am Mac-1a) chain or anti-mouse NK (Ly-49c) antibodies (all from Pharmingen, San Diego, Calif.). These antibodies had been titrated such that the dilution used gave the minimum background staining, typically a 1:50 dilution with blocking buffer. Afterwards, the slides were washed two times with PBS followed by the addition of avidin-biotin complex and diaminobenzidine, according to the manufcture's instructions (Vector, Burlington, Calif.). The sections were washed two times with PBS and counterstained with eosin. After a final wash with xylene, coverslips were placed over the stained sections and mounted with Permount. The distribution of cells that stained with the mAbs was evaluated independently by four investigators and graded quantitatively.

Figure 19:
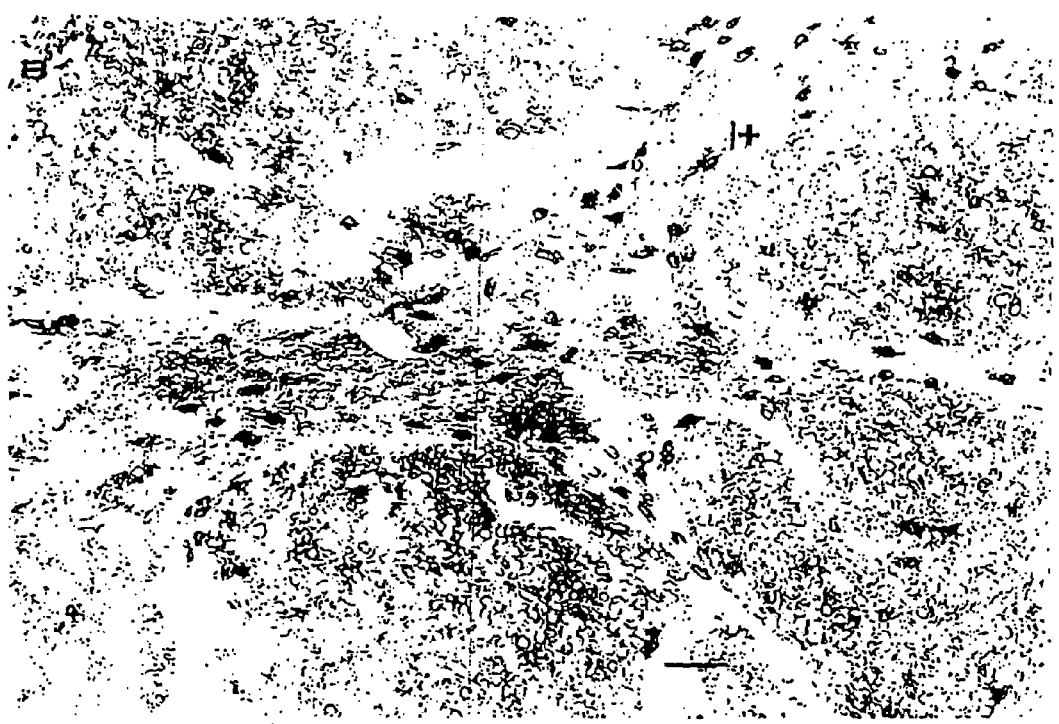
FIG. 19 depicts immunohistochemical staining of breast cancer in mice injected with SB-1 cells and LM-IL-2K$^b$/SB–1 cells. Cells staining with CD8+ mAbs within the epithelium of the tumor are indicated by (◀). + indicates stromal cells lining the epithelial ducts. Horizontal bar=11.0 µm.

As indicated (FIG. 19 and Table V), large numbers of cells reactive with CD8 antibodies infiltrated the epithelial ducts of the breast tumors in mice injected with the mixture of SB-1 and LM-IL-2K$^b$/SB-1 cells. Lesser numbers of CD8$^+$ cells were present in tumors in mice injected with SB-1 cells alone. There were no apparent differences between the numbers of CD4+, CD11b+ or NK cells in breast neoplasms of the treated and untreated groups (Table V).

The same protocol was then followed to charaterize the cellular infiltrates in epithelial ducts of tumors forming in C57BL/6J mice injected with a mixture of EO771 cells and LM-IL-2K$^b$/EO771 cells. Similar CD8+ T cell-infiltrates were present in breast tumors developing in C57BL/6J mice injected with a mixture of EO771 cells and LM-IL-2K$^b$/EO771 cells. Lesser numbers of CD8+ cells were present in tumors developing in mice injected with EO771 cells alone.

TABLE I

CURRENTLY RECOGNIZED HLA SPECIFICITIES DETECTED AT EACH HLA SUBREGION (ROITT ET AL.)

| DR | DQ | DP | B | C | A |
|---|---|---|---|---|---|
| DR1 | Dw1 | DQw1 | DPw1 | Bw4 | Bw47 | Cw1 | A1 |
| DR2 | Dw2 | DQw2 | DPw2 | B5 | Bw48 | Cw2 | A2 |
| DR3 | Dw3 | DQw3 | DPw3 | Bw6 | B49 | Cw3 | A3 |
| DR4 | Dw4 | | DPw4 | B7 | Bw50 | Cw4 | A9 |
| DR5 | | | DPw5 | B8 | B51 | Cw5 | A10 |
| DRw6 | | | DPw6 | B12 | Bw52 | Cw6 | A11 |
| DR7 | Dw7 | | | B13 | Bw53 | Cw7 | Aw19 |
| DRw8 | Dw8 | | | B14 | Bw54 | Cw8 | A23 |
| DRw9 | | | | B15 | Bw55 | | A24 |
| DRw10 | | | | B16 | Bw56 | | A25 |
| DRw11 | Dw5 | | | B17 | Bw57 | | A26 |
| DRw12 | | | | B18 | Bw58 | | A28 |
| DRw13 | Dw6 | | | B21 | Bw59 | | A29 |
| DRw14 | Dw9 | | | Bw22 | Bw60 | | A30 |
| DRw52 | | | | B27 | Bw61 | | A31 |
| DRw53 | | | | B35 | Bw62 | | A32 |
| | | | | B37 | Bw63 | | Aw33 |
| | | | | B38 | Bw64 | | Aw34 |
| | | | | B39 | Bw65 | | Aw36 |
| | | | | B40 | Bw67 | | Aw43 |
| | | | | Bw41 | Bw70 | | Aw66 |
| | | | | Bw42 | Bw71 | | Aw68 |
| | | | | B44 | Bw72 | | Aw69 |
| | | | | B45 | Bw73 | | |
| | | | | B46 | | | |

TABLE II

INTERLEUKIN-2 SECRETION BY GENETICALLY MODIFIED FIBROBLASTS

| VACCINE cell type | IL-2$^a$ (units/10$^6$ cells/48 Hr) |
|---|---|
| LM-ZipNeo | 0 |
| LM-IL-2 | 96 |
| LM-IL-2/B16 | 98 |
| LM-IL-2K$^b$ | 91 |
| LM-IL-2K$^b$/B16 | 86 |

TABLE III

CYTOTOXICITY OF B16 BY SPLEEN CELLS FROM MICE VACCINATED WITH SEMI-ALLOGENEIC FIBROBLASTS TRANSFECTED WITH GENOMIC DNA FROM B16

| VACCINE CELL TYPE | TARGET | AB BLOCKING | SPECIFIC RELEASE |
|---|---|---|---|
| Media | B16 | none | 0.0 |
| | B16 | α CD8$^+$ | 0.0 |
| | B16 | α Asialo-GM1 | 0.0 |
| | c1498 | none | 0.0 |
| LM-ZipNeo | B16 | none | 4.9 ± 1.5 |
| | B16 | α CD8$^+$ | 3.6 ± 1.8 |
| | B16 | α Asialo-GM1 | 1.2 ± .95 |
| | c1498 | none | 2.2 ± .62 |
| LM-IL-2 | B16 | none | 0.0 |
| | B16 | α CD8$^+$ | 0.0 |
| | B16 | α Asialo-GM1 | 0.0 |
| | c1498 | none | 0.0 |
| LM-IL-2/B16* | B16 | none | 2.0 ± .3 |
| | B16 | α CD8$^+$ | 3.3 ± .35 |
| | B16 | α Asialo-GM1 | 1.4 ± 1.4 |
| | c1498 | none | 3.1 ± 2.1 |
| LM-IL-2K$^b$ | B16 | none | 6.3 ± 2.1 |
| | B16 | α CD8$^+$ | 2.0 ± 1.7 |

TABLE III-continued

CYTOTOXICITY OF B16 BY SPLEEN CELLS FROM MICE VACCINATED WITH SEMI-ALLOGENEIC FIBROBLASTS TRANSFECTED WITH GENOMIC DNA FROM B16

| VACCINE CELL TYPE | TARGET | AB BLOCKING | SPECIFIC RELEASE |
|---|---|---|---|
| | B16 | α Asialo-GM1 | 3.3 ± .75 |
| | c1498 | none | 4.8 ± 2.4 |
| LM-IL-2K$^b$/B16** | B16 | none | 19.1 ± .36 |
| | B16 | α CD8$^+$ | 9.3 ± 2.0 |
| | B16 | α Asialo-GM1 | 17.6 ± 2.7 |
| | c1498 | none | 3.8 ± 1.6 |

TABLE IV

CYTOTOXIC RESPONSES TOWARD EO771 BREAST CARCINOMA CELLS IN C57BL/6J MICE INJECTED WITH A MIXTURE OF EO771 CELLS AND LM-IL-2K$^b$/EO771 CELLS

| Injected with EO771 cells | Target | % specific |
|---|---|---|
| $^{51}$Cr-release and LM-IL-2K$^b$/EO771 cells | EO771 | 25.0 ± 7 |
| LM cells | EO771 | 9.0 ± 4 |
| LM-IL-2K$^b$ cells | EO771 | 3.1 ± 2.0 |
| LM-IL-2K$^b$/B16 cells | E0771 | 7.0 ± 4.0 |
| Media | E0771 | 3.3 ± 1.0 |
| EO771 cells and LM-IL-2K$^b$/EO771 cells | LM | 59 ± 12 |
| LM cells | LM | 64 ± 15 |
| LM-IL-2K$^b$ cells | LM | 53 ± 3 |
| LM-IL-2K$^b$/B16 cells | LM | 57 ± 10 |
| Media | LM | 1.8 ± 12 |

Legend to Table IV:
C57BL/6J mice were injected into the fat pad of the breast with a mixture of $5 \times 10^3$ EO771 cells and $2 \times 10^6$ LM-IL-2K$^b$/EO771 cells or with equivalent numbers of EO771 cells and LM cells, EO771 cells and LM-IL-2K$^b$ cells, with EO771 cells and LM-IL-2K$^b$/B16 cells, or with EO771 cells in growth media. The mice received two subsequent injections i.p. and into the breast of equivalent numbers of LM cells, LM-IL-2K$^b$ cell, or LM-IL-2K$^b$/B16 cells, without additional EO771 cells. One week after the last injection, the mice were killed, and pooled spleen cell-suspensions from mice in each group were mixed with mitomycin C-treated (50 ug/ml for 30 min. at 37° C.) stimulator cells of the same type used to immunize the mice, followed by incubation at 37° C. under standard cell culture conditions for five days. At the end of the incubation, a $^{51}$Cr-release assay was performed, using $^{51}$Cr-labeled EO771 cells or $^{51}$Cr-labeled LM cells as "targets" the reaction. The ratio of spleen cells to target cells was 100:1.

TABLE V

IMMUNOHISTOCHEMICAL STAINING OF BREAST NEOPLASMS IN MICE INJECTED WITH SB-1 CELLS AND LM-IL-2K$^b$/SB-1 CELLS

| | Infiltrating Cells | | | |
|---|---|---|---|---|
| | CD4 | CD8 | CD11b | NK |
| Injected with SB-1 and LM-IL-2K$^b$/SB-1 cells | 1.1 ± 0.9 | 9.9 ± 3.4 | 6.5 ± 3.0 | 0.4 ± 0.5 |

TABLE V-continued

IMMUNOHISTOCHEMICAL STAINING OF BREAST NEOPLASMS IN MICE INJECTED WITH SB-1 CELLS AND LM-IL-2K$^b$/SB-1 CELLS

| | Infiltrating Cells | | | |
|---|---|---|---|---|
| | CD4 | CD8 | CD11b | NK |
| Injected with SB-1 cells alone | 2.0 ± 1.6 | 0.9 ± 1.4 | 8.0 ± 2.0 | <0.1 ± 0.1 |

Legend:
C3H/HeJ mice were injected into the fat pad of the breast with a mixture of $1 \times 10^6$ SB-1 cells and $2 \times 10^6$ LM-IL-2K$^b$/SB-1 cells in a total volume of 200 μl. At the same time the mice received an injection i.p. of $2 \times 10^6$ LM-IL-2K$^b$/SB-1 cells in 200 μl alone, followed by two subsequent injections at weekly intervals of $2 \times 10^6$ LM-IL-2K$^b$/SB-1 cells i.p. and $2 \times 10^6$ LM-IL-2K$^b$/SB-1 cells into the fat pad of the same breast as first injected. As controls, other naive C3H/He mice were injected according to the same protocol with equivalent numbers of SB-1 cells into the breast alone, without subsequent injections. One week after the last injection, histologic sections were prepared for immunohistochemical staining with CD4, CD8, CD11b or NK mAbs. The data represent an examination of cell numbers in five high powered fields per each of eight slides by three independent observers.
P < .001 for difference in number of CD8+ cells in tumors of mice injected with SB-1 cells and LM-IL-2K$^b$/SB-1 cells and mice injected with SB-1 cells alone.
P for difference in number of CD4+, CD11b or NK cells in tumors of mice injected with SB-1 cells and LM-IL-2K$^b$/SB-1 cells and mice injected with SB-1 cells alone, not significant.

What is claimed is:

1. A method of treating a tumor in an animal which comprises administering to said animal a tumor inhibiting effective amount of an antigen-presenting cell, wherein said antigen-presenting cell expresses at least one class I MHC or class II MHC determinant that is syngeneic to said animal and at least one class I or II MHC determinant that is allogeneic to said animal, wherein said antigen-presenting cell is selected from the group consisting of professional antigen-presenting cells and facultative antigen-presenting cells, and wherein said antigen-presenting cell is transfected with total genomic DNA isolated from the tumor cells of said animal.

2. The method according to claim 1, wherein said antigen presenting cell is further transfected with a nucleic acid molecule coding for at least one cytokine.

3. The method of claim 2, wherein said cytokine is selected from the group consisting of interleukin-1, interleukin-2, interleukin-3, interleukin-4, interleukin-5, interleukin-6, interleukin-7, interleukin-8, interleukin-9, interleukin-10, interleukin-11, interleukin-12, interferon-α, interferon-γ, tumor necrosis factor, granulocyte macrophage colony stimulating factor, and granulocyte colony stimulating factor.

4. The method according to claim 1, wherein said antigen-presenting cell is selected from the group consisting of a fibroblast, a macrophage, a B cell, and a dendritic cell.

5. The method according to claim 1, wherein said tumor is a solid tumor or a hematological tumor.

6. The method of claim 5, wherein said tumor is selected from the group consisting of melanoma, lymphoma, plasmacytoma, sarcoma, glioma, thymoma, leukemias, breast cancer, prostate cancer, colon cancer, esophageal cancer, brain cancer, lung cancer, ovarian cancer, cervical cancer and hepatoma.

7. The method according to claim 1, wherein said animal is a human subject.

8. A method of inhibiting tumor cell growth in an animal which comprises administering to said animal a tumor-inhibiting effective amount of an antigen-presenting cell, wherein said antigen presenting cell expresses at least one class I MHC or class II MHC determinant that is syngeneic to said animal and at least one class I or II MHC determinant that is allogeneic to said animal, wherein said antigen-presenting cell is selected from the group consisting of professional antigen-presenting cells and facultative antigen-presenting cells, and wherein said antigen-presenting cell is transfected with total genomic DNA isolated from the tumor cells of said animal.

9. The method of claim 8, wherein said antigen presenting cell is further transfected with a nucleic acid molecule coding for at least one cytokine.

10. The method of claim 8, wherein said cytokine is selected from the group consisting of interleukin-1, interleukin-2, interleukin-3, interleukin-4, interleukin-5, interleukin-6, interleukin-7, interleukin-8, interleukin-9, interleukin-10, interleukin-11, interleukin-12, interferon-$\alpha$, interferon-$\gamma$, tumor necrosis factor, granulocyte macrophage colony stimulating factor, and granulocyte colony stimulating factor.

11. The method of claim 8, wherein said antigen-presenting cell is selected from the group consisting of a fibroblast, a macrophage, a B cell, and a dendritic cell.

12. The method of claim 8, wherein said tumor is a solid tumor or a hematological tumor.

13. The method of claim 8, wherein said tumor is selected from the group consisting of melanoma, lymphoma, plasmacytoma, sarcoma, glioma, thymoma, leukemias, breast cancer, prostate cancer, colon cancer, esophageal cancer, brain cancer, lung cancer, ovarian cancer, cervical cancer and hepatoma.

14. The method of claim 8, wherein said animal is a human subject.

15. The method of claim 1, wherein said total genomic DNA is sheared.

* * * * *

UNITED STATES PATENT AND TRADEMARK OFFICE
CERTIFICATE OF CORRECTION

PATENT NO.         : 7,402,306 B1              Page 1 of 1
APPLICATION NO.    : 09/522716
DATED              : July 22, 2008
INVENTOR(S)        : Edward P. Cohen It is certified that error appears in the above-identified patent and that said Letters Patent is hereby corrected as shown below:

At Column 1, line 18, please delete "may have" and add --has--.

Signed and Sealed this

Eighth Day of December, 2009

David J. Kappos
*Director of the United States Patent and Trademark Office*